United States Patent
Saji et al.

(10) Patent No.: US 9,849,197 B2
(45) Date of Patent: Dec. 26, 2017

(54) SWITCHING-TYPE FLUORESCENT NANOPARTICLE PROBE, AND FLUORESCENT MOLECULAR IMAGING METHOD USING SAME

(75) Inventors: Hideo Saji, Kyoto (JP); Shunsaku Kimura, Hirakata (JP); Masahiro Ono, Uji (JP); Takashi Temma, Kyoto (JP); Isao Hara, Kyoto (JP); Eiichi Ozeki, Kyoto (JP)

(73) Assignees: KYOTO UNIVERSITY, Kyoto (JP); SHIMADZU CORPORATION, Kyoto (JP)

( * ) Notice: Subject to any disclaimer, the term of this patent is extended or adjusted under 35 U.S.C. 154(b) by 1155 days.

(21) Appl. No.: 14/002,327

(22) PCT Filed: Mar. 1, 2012

(86) PCT No.: PCT/JP2012/055168
§ 371 (c)(1),
(2), (4) Date: Aug. 29, 2013

(87) PCT Pub. No.: WO2012/118136
PCT Pub. Date: Sep. 7, 2012

(65) Prior Publication Data
US 2013/0336896 A1    Dec. 19, 2013

(30) Foreign Application Priority Data

Mar. 2, 2011 (JP) .................. 2011-044841
Aug. 18, 2011 (JP) .................. 2011-179252

(51) Int. Cl.
*A61K 9/00*        (2006.01)
*A61K 49/00*       (2006.01)

(52) U.S. Cl.
CPC ...... *A61K 49/0054* (2013.01); *A61K 49/0032* (2013.01); *A61K 49/0034* (2013.01); *A61K 49/0069* (2013.01); *A61K 49/0093* (2013.01)

(58) Field of Classification Search
CPC .................................................. A61K 49/0054
See application file for complete search history.

(56) References Cited

U.S. PATENT DOCUMENTS 6,083,486 A      7/2000 Weissleder et al.
2004/0022731 A1  2/2004 Bogdanov et al.
(Continued)

FOREIGN PATENT DOCUMENTS

EP    2 305 214 A1    4/2011
EP    2 609 935 A1    7/2013
(Continued)

OTHER PUBLICATIONS

Supplementary European Search Report for the Application No. EP 12 75 1966 dated Aug. 20, 2014.
(Continued)

*Primary Examiner* — Paul Dickinson
(74) *Attorney, Agent, or Firm* — Cheng Law Group, PLLC

(57) ABSTRACT

[Problem] To provide a novel fluorescent nanoparticle imaging probe having a switching function (a function to quench a fluorescent dye in a blood component and emit fluorescence in a tumor or an inflamed site to be imaged).
[Solution] A fluorescent nanoparticle probe comprising: a molecular assembly composed of an amphiphilic block polymer having a hydrophilic block chain and a hydrophobic block chain; and a fluorescent dye encapsulated in the assembly, wherein (a) the hydrophilic block chain comprises, as an essential hydrophilic structural unit, a unit
(Continued)

selected from a sarcosine unit and an alkylene oxide unit, (b) the hydrophobic block chain comprises, as an essential hydrophobic structural unit, a unit selected from the group consisting of an amino acid unit and a hydroxylic acid unit, and (c) the fluorescent dye is a polylactic acid-bound cyanine compound comprising: a fluorescent group represented by the formula (I):

[Chemical Formula 1]

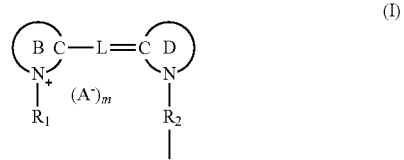

(I)

and a polylactic acid group having 5 to 50 lactic acid units, and two or more molecules of the fluorescent dye are encapsulated in the single molecular assembly.

17 Claims, 10 Drawing Sheets

(56) References Cited

U.S. PATENT DOCUMENTS

| 2008/0019908 | A1 | 1/2008 | Akitsu et al. |
| 2011/0104056 | A1 | 5/2011 | Hara et al. |

FOREIGN PATENT DOCUMENTS

| JP | 2005-220045 A | 8/2005 |
| JP | 2005-523945 A | 8/2005 |
| JP | 2008-24816 A | 2/2008 |
| WO | WO-2009/148121 A1 | 12/2009 |
| WO | WO-2012/026316 A1 | 3/2012 |

OTHER PUBLICATIONS

Written Opinion of the International Searching Authority (PCT/ISA/237) for Application No. PCT/JP2012/055168 dated Sep. 12, 2013.
International Search Report for the Application No. PCT/JP2012/055168 dated Apr. 10, 2012.
Mujumdar, Swati et al., "Cyanine-Labeling Reagents: Sulfobenzindocyanine Succinimidyl Esters", Bioconjugate Chem., 1996, vol. 7, No. 3, pp. 356-362.
Yoichi, Shimizu et al., The Pharmaceutical Society of Japan, Mar. 29, 2010, 130, poster 29P-am395Q.
Makino, Akira et al., "Preparation of Novel Polymer Assemblies, 'Lactosome', Composed of Poly(L-lactic acid) and Poly(sarcosine)", Chemistry Letters, 2007, vol. 36, No. 10, pp. 1220-1221.
Kidchob, Tongjit et al., "Amphiphilic poly(Ala)-b-poly(Sar) microspheres loaded with hydrophobic drug", Journal of Controlled Release, 1998, vol. 51, pp. 241-248.
Tung, Ching-Hsuan et al., "In Vivo Imaging of Proteolytic Enzyme Activity Using a Novel Molecular Reporter", Cancer Research, Sep. 1, 2000, vol. 60, pp. 4953-4958.
Lin, Yuhul et al., "Novel Near-Infrared Cyanine Fluorochromes: Synthesis, Properties, and Bioconjugation", Bioconjugate Chem., 2002, vol. 13, pp. 605-610.
Ogawa, Mikako et al., "In Vivo Molecular Imaging of Cancer with a Quenching Near-Infrared Fluorescent Probe Using Conjugates of Monoclonal Antibodies and Indocyanine Green", Cancer Res., Feb. 15, 2009, vol. 69, No. 4, pp. 1268-1272.
Tatsuya et al., "Novel Nano-Carrier 'Peptosome': Coming Materials for the Next Generation DDS", Kagaku to Seibutsu, Nov. 1, 2007, vol. 45, No. 11, pp. 779-784.
New Energy and Industrial Technology Development Organization, Achievement Reports 2009, Jun. 18, 2010, p. 52, lines 2-13.
Sasatsu, Masanao et al., "Hyoushikitai PLA-Pyrene no Gosei to PLA Yudotai Nanoparticle no Ryushi Tokusei", Journal of Pharmaceutical Science and Technology, Japan, Apr. 30, 2008, vol. 68, Supplement, p. 281.
Ozeki, Eiichi et al., "Development of novel tumor-accumulating nanoparticle 'Lactosome'", Bio Clinca. Nov. 10, 2011, vol. 26, No. 12, pp. 1112-1115.

Fig.5 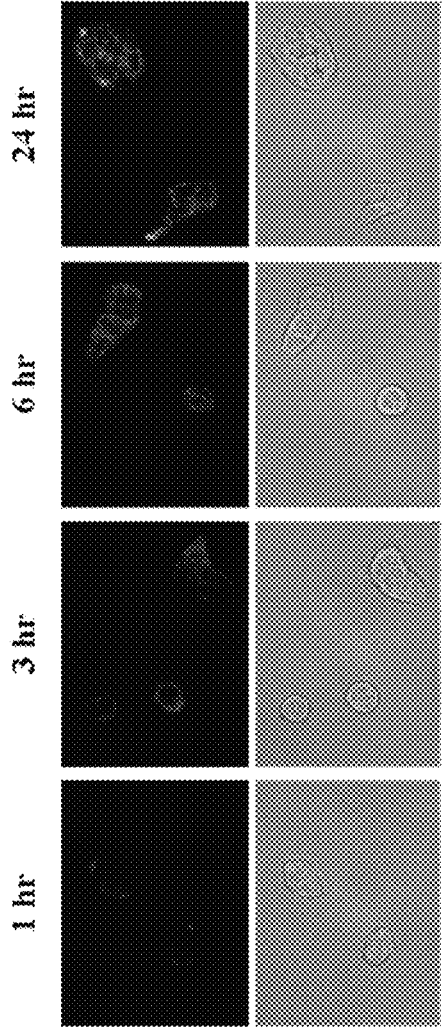 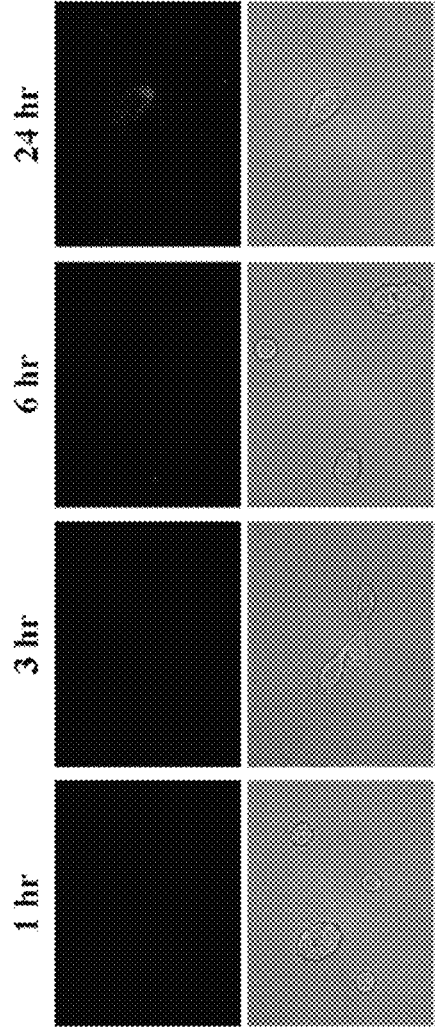

Fig.6
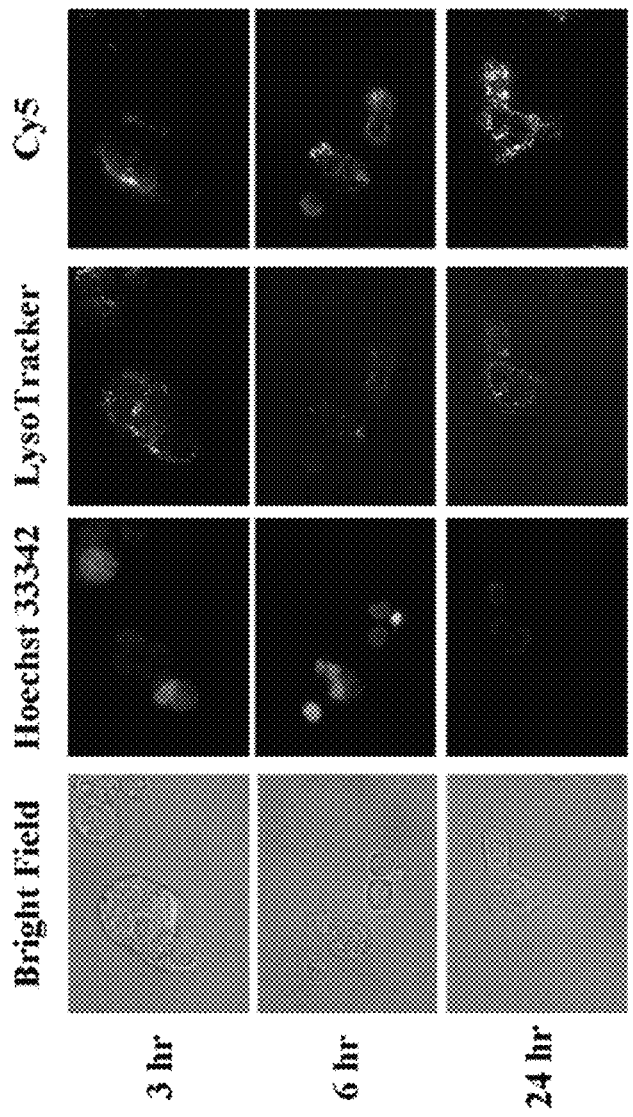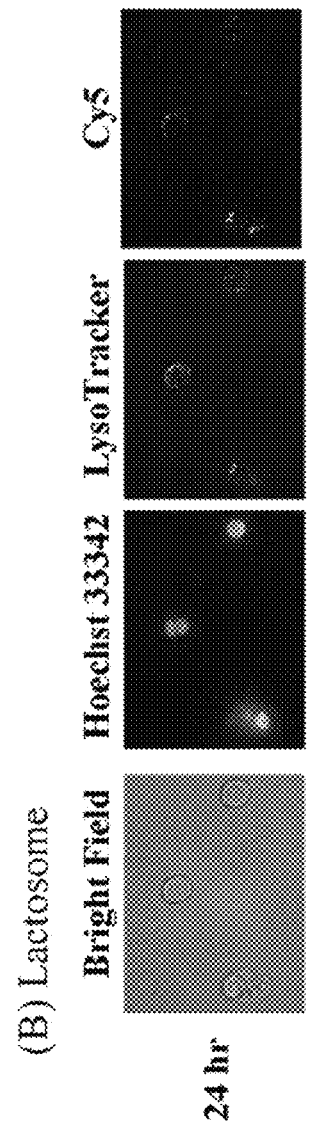

Fig. 7
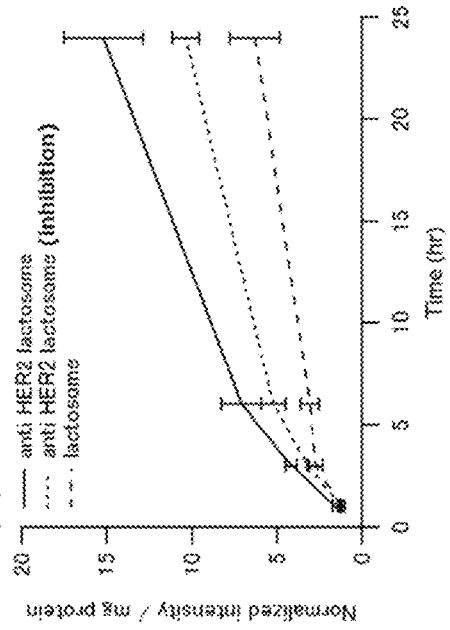
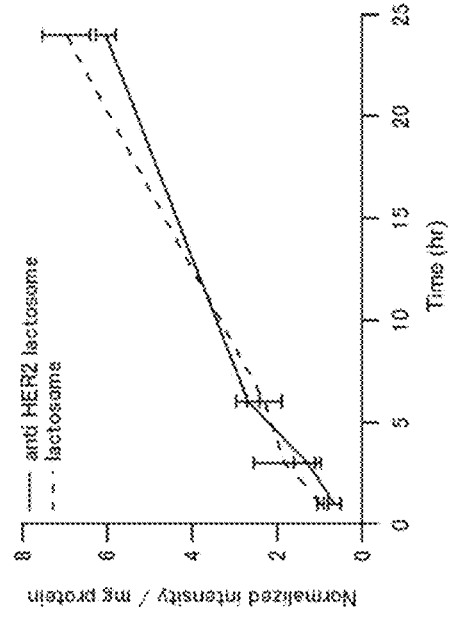
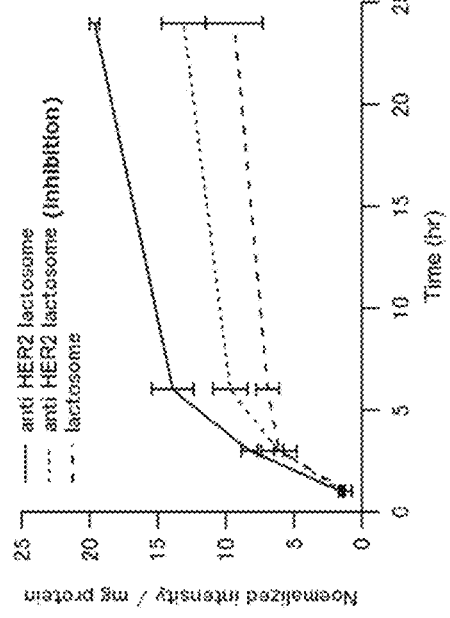
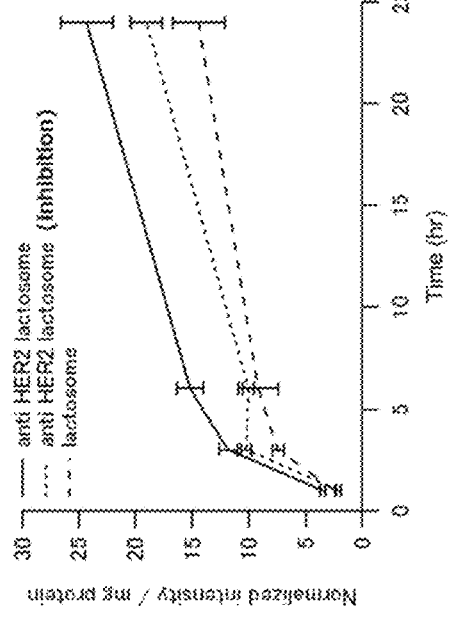

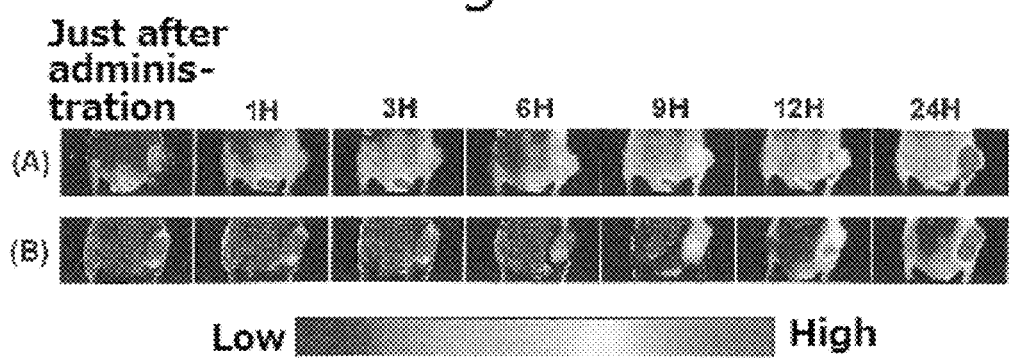

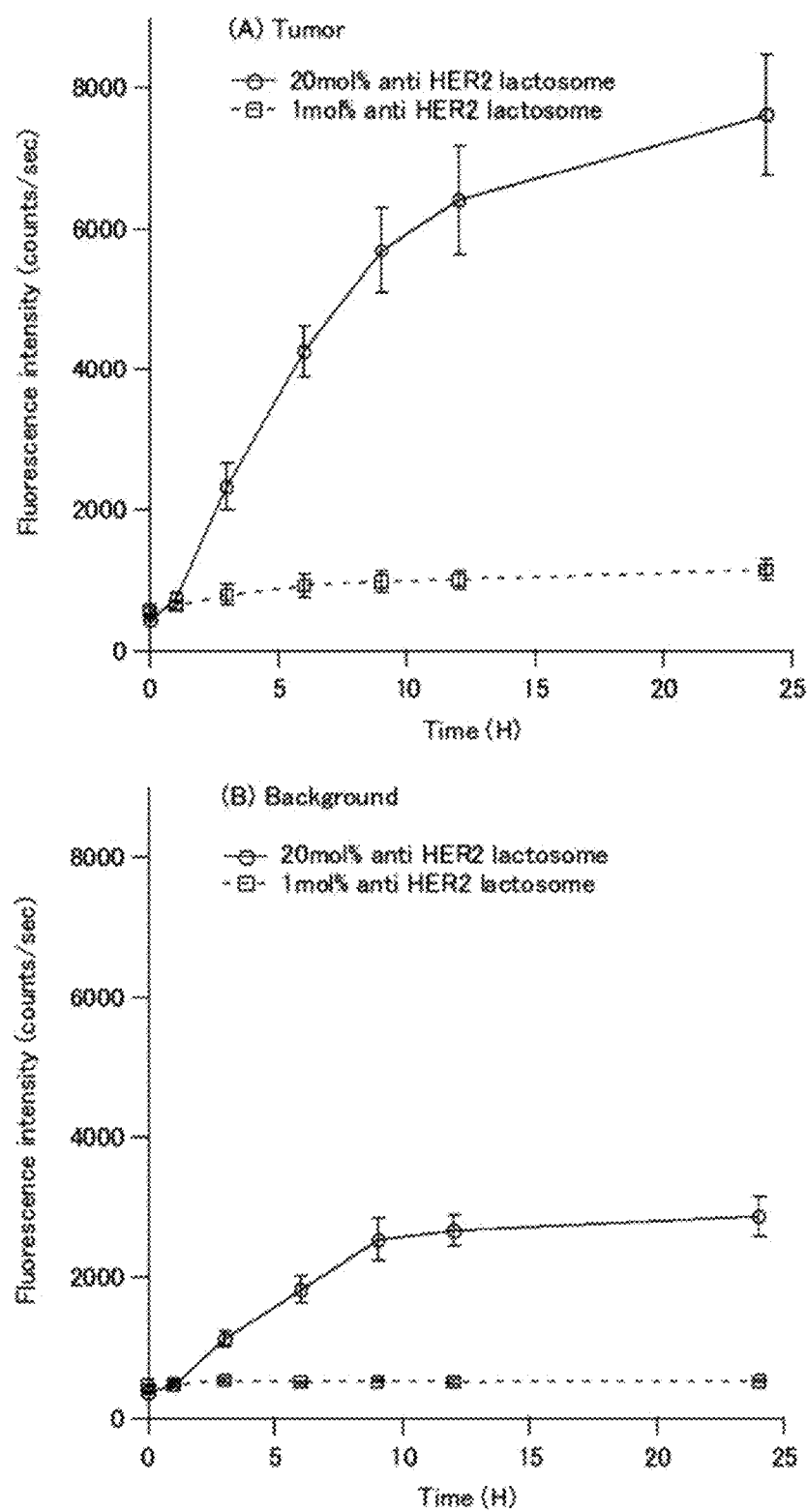

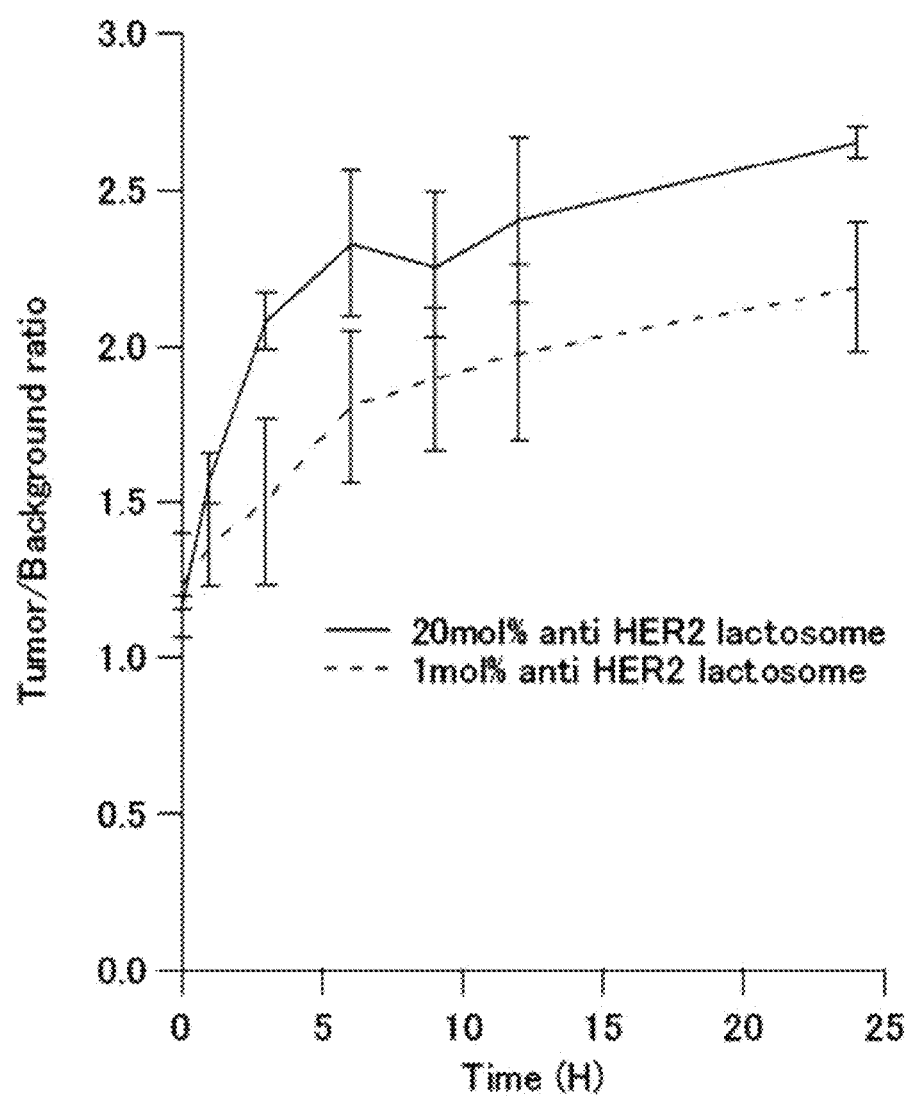

SWITCHING-TYPE FLUORESCENT NANOPARTICLE PROBE, AND FLUORESCENT MOLECULAR IMAGING METHOD USING SAME

TECHNICAL FIELD

The present invention relates to a fluorescent nanoparticle comprising a molecular assembly composed of an amphiphilic substance having biocompatibility and a fluorescent dye encapsulated in the molecular assembly, and fluorescence imaging using the fluorescent nanoparticle as a probe.

BACKGROUND ART

In recent years, there has been increasing interest in nanotechnology, and novel functional materials utilizing properties unique to nanosized substances have been developed. Such novel functional materials can be applied to a wide variety of fields such as energy, electronics, and medical and pharmaceutical fields. Among them, nanotechnology has received attention for the detection of substances in biological samples and in vivo imaging.

In medical and pharmaceutical fields, attention has been given to a near-infrared fluorescence photography method for imaging a tumor site by accumulation of a near-infrared fluorescent dye in the tumor site. In this method, a compound having the property of emitting fluorescence in the near-infrared region by irradiation with excitation light is administered as an imaging agent to a living body. Then, the living body is externally irradiated with excitation light in having a near-infrared wavelength, and fluorescence emitted from the fluorescent imaging agent accumulated in a tumor site is detected to determine a lesion site.

A substance used as an imaging probe is mainly composed of a carrier agent and a fluorescent dye, and various carrier agents and fluorescent dyes have been reported.

Examples of the carrier agent include a liposome nanoparticle (JP-A-2005-220045 (Patent Document 1)), a peptidic nanoparticle (Journal of Controlled Release 51 (1998) 241-248 (Non-Patent Document 1)), a nanoparticle using an amphiphilic block polymer having, as a hydrophobic block, poly glutamic acid methyl ester (JP-A-2008-024816 (Patent Document 2)), a nanoparticle using an amphiphilic block polymer composed of a polysarcosine chain and a polylactic acid chain (Chemistry Letters, vol. 36, no. 10, 2007, p. 1220-1221 (Non-Patent Document 2)), and a nanoparticle using an amphiphilic block polymer composed of a polysarcosine chain and a polylactic acid chain, and a polylactic acid (WO 2009/148121 (Patent Document 3)).

The fluorescent dye is covalently bound to or non-covalently encapsulated in the carrier agent, and a fluorescein-based dye, a cyanine-based dye, a rhodamine-based dye, or the like is used. As the cyanine-based dye, indocyanine green (ICG) is often used, but various indocyanine derivatives have been developed (Bioconjugate Chem. 1996, 7, 356-362 (Non-Patent Document 3), The 131st Annual Meeting of The Pharmaceutical Society of Japan, 29p-am395Q poster, Mar. 29, 2010 (Non-Patent Document 4)). Further, methods have been reported which allow nanoparticles quenched by encapsulation of both an indocyanine derivative and a quencher to acquire fluorescence when the nanoparticles reach a tumor tissue (Cancer Research, 60, 4953-4958, Sep. 1, 2000 (Non-Patent Document 5), Bioconjugate Chem. 2002, 13, 605-610 (Non-Patent Document 6), Cancer Research, 2009; 69: (4). Feb. 15, 2009 (Non-Patent Document 7)).

More specifically, Non-Patent Document 4 described above discloses the preparation of nanoparticles IC7-1 lactosome from 500 μL of a 6 mg/mL solution of an amphiphilic polymer composed of a polysarcosine chain and a polylactic acid chain ($PSar_{70}$-$PLLA_{30}$), and 3.16 μL of a 1 mg/mL solution of an indocyanine derivative IC7-1. That is, it has been disclosed that the amount of the indocyanine derivative IC7-1 encapsulated in the nanoparticle IC7-1 lactosome is 0.48 mol %. This amount of the encapsulated indocyanine derivative IC7-1 corresponds to 1 molecule per single nanoparticle IC7-1 lactosome.

CITATION LIST

Patent Documents

Patent Document 1: JP-A-2005-220045
Patent Document 2: JP-A-2008-024816
Patent Document 3: WO 2009/148121

Non-Patent Documents

Non-Patent Document 1: "Journal of Controlled Release", Vol. 51, 1998, pp. 241-248
Non-Patent Document 2: "Chemistry Letters", Vol. 36, No. 10, 2007, pp. 1220-1221
Non-Patent Document 3: "Bioconjugate Chemistry", 1996, Vol. 7, pp. 356-362
Non-Patent Document 4: The 131st Annual Meeting of The Pharmaceutical Society of Japan, 29p-am395Q poster, Mar. 29, 2010
Non-Patent Document 5: "Cancer Research", Vol. 60, pp. 4953-4958, Sep. 1, 2000
Non-Patent Document 6: "Bioconjugate Chemistry", 2002, Vol. 13, pp. 605-610
Non-Patent Document 7: "Cancer Research", 2009; Vol. 69: (No. 4), Feb. 15, 2009

SUMMARY OF THE INVENTION

Problems to be Solved by the Invention

It is an object of the present invention to provide a novel fluorescent nanoparticle imaging probe having a switching function (a function to quench a fluorescent dye during nanoparticle preparation and in a blood component and emit fluorescence in a tumor or an inflamed site to be imaged).

Means for Solving the Problems

The present inventors have already found that a self-quenching nanoparticle by encapsulating a high concentration of a cyanine-based fluorescent compound has the extraordinary effect of recovering fluorescence intensity by contact with a blood component. The present inventors have further intensively studied, and as a result have further found that a self-quenching nanoparticle by encapsulating a high concentration of a polylactic acid-bound cyanine-based fluorescent compound has such a more extraordinary effect that said self-quenching nanoparticle remains self-quenching state even by contact with a blood component, but recovers fluorescence intensity by contact with or incorporation into a cell. This finding has led to the completion of the present invention.

The present invention includes the following switching-type fluorescent nanoparticle probe and imaging method using the same.

(1) A fluorescent nanoparticle probe comprising:
a molecular assembly composed of an amphiphilic block polymer having a hydrophilic block chain and a hydrophobic block chain; and
a fluorescent dye encapsulated in the molecular assembly, wherein
(a) the hydrophilic block chain comprises, as an essential hydrophilic structural unit, a unit selected from a sarcosine unit and an alkylene oxide unit, and has the 20 or more essential hydrophilic structural units,
(b) the hydrophobic block chain comprises, as an essential hydrophobic structural unit, a unit selected from the group consisting of an amino acid unit and a hydroxylic acid unit, and has the 15 or more essential hydrophobic structural units, and
(c) the fluorescent dye is a polylactic acid-bound cyanine compound comprising:
a fluorescent group represented by the following structural formula (I):

[Chemical Formula 1]

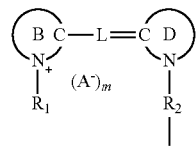

(I)

wherein $R_1$ is a hydrocarbon group which may be substituted, and $R_2$ is a bivalent hydrocarbon group which may be substituted; $A^-$ is an anion and m is 0 or 1; a ring B and a ring D may be the same or different from each other and each is a nitrogen-containing heterocycle; and L is a linking group that constitutes a polymethine chain, which may include a ring structure, and which may be substituted; and
a polylactic acid group having 5 to 50 lactic acid units, and
two or more molecules of the fluorescent dye are encapsulated in the single molecular assembly.
In the above-described switching-type fluorescent nanoparticle probe, fluorescence is quenched by the association of two or more molecules of the encapsulated fluorescent dye.
(2) The fluorescent nanoparticle probe according to (1), wherein the fluorescent dye is encapsulated in the molecular assembly in an amount of 1 to 50 mol % with respect to a total amount of the amphiphilic block polymer and the fluorescent dye.
The above-described amount of the fluorescent dye encapsulated in the fluorescent nanoparticle corresponds to 2 to 200 molecules of the fluorescent dye per particle.
(3) The fluorescent nanoparticle probe according to (1) or (2), wherein fluorescence intensity when brought into contact with or incorporated into a cell is 10 times or more higher than that when brought into contact with a blood component.
One example of the case where the fluorescence intensity increases 10 times includes a case where the amount of the encapsulated fluorescent dye is 20 mol % (i.e., corresponding to 50 molecules of the fluorescent dye per fluorescent nanoparticle). The fluorescence intensity of the fluorescent nanoparticle probe increases by adding the fluorescent nanoparticle probe to cells and can reach 10 times or more 24 hours after the addition.
(4) The fluorescent nanoparticle probe according to any one of (1) to (3), wherein the linking group represented by L has either of the following structures:

[Chemical Formula 2]

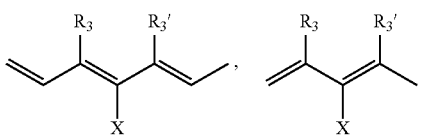

wherein $R_3$ and $R_3'$ are hydrogen or are linked together to form the ring structure; and X is hydrogen or a halogen.
(5) The fluorescent nanoparticle probe according to any one of (1) to (4), wherein the ring B has either of the following structures:

[Chemical Formula 3]

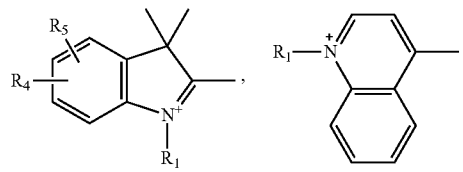

wherein $R_1$ is a hydrocarbon group which may be substituted; and $R_4$ and $R_5$ are each hydrogen or an anionic substituent group, or are linked together to form an aryl ring, and
the ring D has either of the following structures:

[Chemical Formula 4]

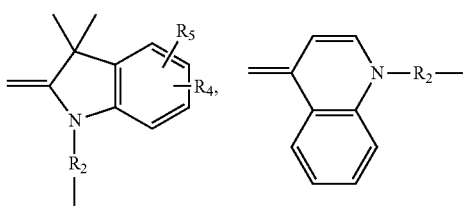

wherein $R_2$ is a bivalent hydrocarbon group which may be substituted; and $R_4$ and $R_5$ are each hydrogen or an anionic substituent group, or are linked together to form an aryl ring.
(6) The fluorescent nanoparticle probe according to any one of (1) to (5), wherein the fluorescent group is represented by the following structural formula (II):

[Chemical Formula 5]

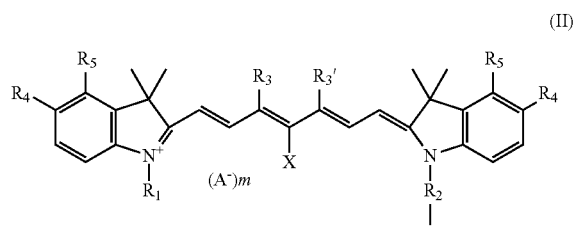

(II)

wherein $R_1$ is a hydrocarbon group which may be substituted, $R_2$ is a bivalent hydrocarbon group which may be substituted; $R_3$ and $R_3'$ are hydrogen or are linked together to form a ring structure; X is hydrogen or a halogen; $A^-$ is an anion and m is 0 or 1; a ring B and a ring D may be the same or different from each other and each is a nitrogen-containing condensed aromatic heterocycle; and $R_4$ and $R_5$ are each hydrogen or an anionic substituent group or are linked together to form an aryl ring.

(7) The fluorescent nanoparticle probe according to any one of (1) to (6), wherein the fluorescent group is represented by the following structural formula (III):

[Chemical Formula 6]

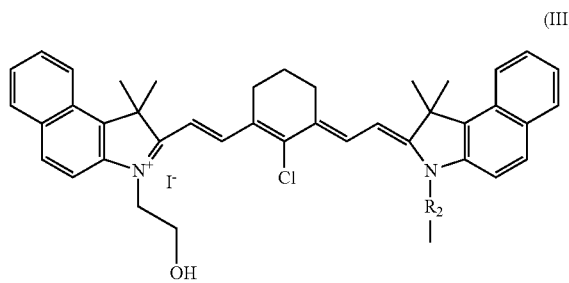

(III)

wherein $R_2$ is a bivalent hydrocarbon group which may be substituted.

(8) The fluorescent nanoparticle probe according to any one of (1) to (6), wherein the fluorescent group is represented by the following structural formula (IV):

[Chemical Formula 7]

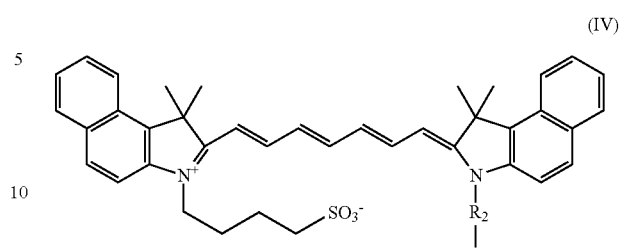

(IV)

wherein $R_2$ is a bivalent hydrocarbon group which may be substituted.

(9) The fluorescent nanoparticle probe according to any one of (1) to (3), wherein the fluorescent group is represented by the following formula (X):

[Chemical Formula 8]

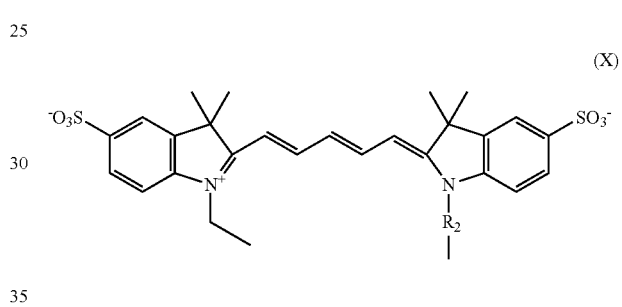

(X)

wherein $R_2$ is a bivalent hydrocarbon group which may be substituted.

(10) The fluorescent nanoparticle probe according to any one of (1) to (6), wherein the fluorescent dye is represented by the following formula (III-i):

[Chemical Formula 9]

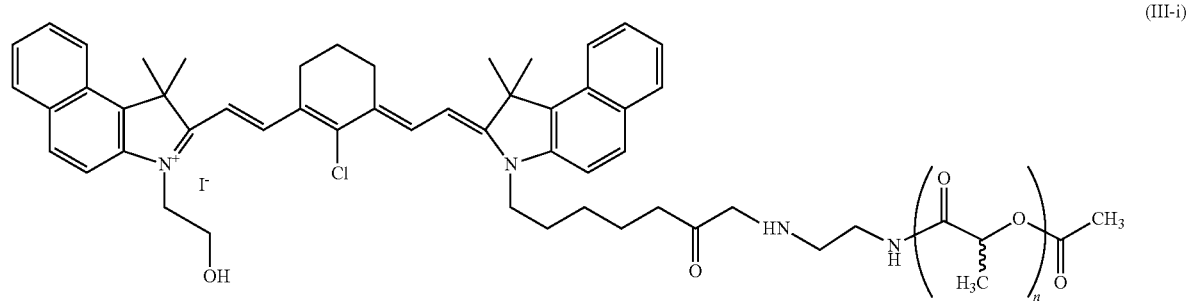

(III-i)

wherein n is an integer of 5 to 50.

(11) The fluorescent nanoparticle probe according to any one of (1) to (6), wherein the fluorescent dye is represented by the following formula (IV-i):

[Chemical Formula 10]

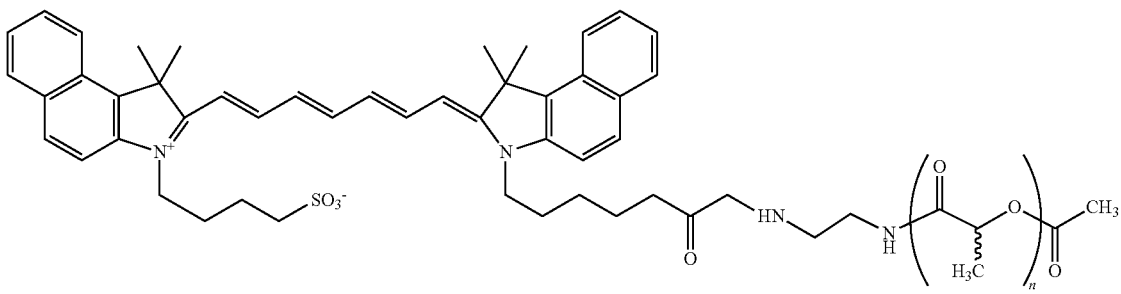

(IV-i)

wherein n is an integer of 5 to 50.

(12) The fluorescent nanoparticle probe according to any one of (1) to (4), wherein the fluorescent dye is represented by the following formula (X-i):

[Chemical Formula 11]

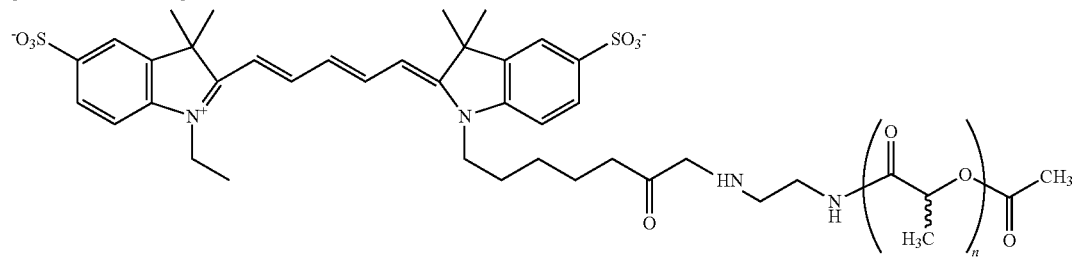

(X-i)

wherein n is an integer of 5 to 50.

(13) The fluorescent nanoparticle probe according to any one of (1) to (12), wherein the hydrophobic block chain is selected from the group consisting of:
 a hydrophobic polypeptide chain having 10 or more hydrophobic amino acid units,
 a hydrophobic polyester chain having 15 or more hydroxylic acid units, and
 a hydrophobic depsipeptide chain having a total of 20 or more units of both an amino acid unit and a hydroxylic acid unit.

(14) The fluorescent nanoparticle probe according to any one of (1) to (13), wherein the hydrophobic block chain is a hydrophobic block chain having 25 or more lactic acid units.

(15) The fluorescent nanoparticle probe according to any one of (1) to (14), wherein the hydrophilic block chain has an antibody, and a surface of the probe is modified with the antibody.

(16) The fluorescent nanoparticle probe according to (15), wherein the antibody is an antibody against a substance contained in a tumor.

(17) A fluorescent molecular imaging method comprising the steps of:
 administering the fluorescent nanoparticle probe according to any one of (1) to (16) to a non-human animal; and
 detecting fluorescence.

Effects of the Invention

According to the present invention, it is possible to provide a novel fluorescent nanoparticle imaging probe having a switching function (i.e., a function to quench a fluorescent dye in blood and emit fluorescence in a tumor or an inflamed site to be imaged).

More specifically, according to the present invention, it is possible to provide a nanoparticle which encapsulates a polylactic acid-bound cyanine compound as a fluorescent dye to be encapsulated and whose fluorescent dye content is made higher than that of a conventional nanoparticle so that the fluorescence of the encapsulated fluorescent dye is reduced dependently upon concentration (of the fluorescent dye) during preparation and in an environment containing a blood component, and the fluorescence is recovered by contact with a cell component; said nanoparticle being excellent in accumulation in a desired tissue by EPR effect. Therefore, it is possible to provide a fluorescent nanoparticle probe that emits high-intensity fluorescence specifically in a desired tissue in a living body, and a fluorescence imaging method using the same.

BRIEF DESCRIPTION OF THE DRAWINGS

FIG. 1 shows the measurement results of fluorescence intensity of ICG-PLLA-encapsulating lactosomes (at an ICG concentration of 0.48 μM) obtained in Example 2, wherein FIG. 1(A) shows the fluorescence intensities of the lactosomes each encapsulating 0.6, 1, 1.5, 2, 3, 4, or 8 mol % of ICG-PLLA$_{30}$, FIG. 1(B) shows the fluorescence intensities of the lactosomes each encapsulating 0.6, 1, 1.5, 2, 3, 4, or 8 mol % of ICG-PLLA$_{32}$, and FIG. 1(C) shows the fluorescence intensities of the lactosomes at 817 nm.

FIG. 5 shows the results of fluorescence microscope observation obtained in Example 5-2, when an antibody-modified lactosome encapsulating 1 mol % of Cy5-PLLA$_{30}$ (Cy5 anti HER2 lactosome) and an antibody-unmodified lactosome encapsulating 1 mol % of Cy5-PLLA$_{30}$ (Cy5 lactosome) were brought into contact with or incorporated into cells, respectively.

FIG. 6 shows the results of fluorescence microscope observation obtained in Example 5-3, when an antibody-modified lactosome encapsulating 20 mol % of Cy5-PLLA$_{30}$ (Cy5 anti HER2 lactosome) and an antibody-unmodified lactosome encapsulating 20 mol % of Cy5-PLLA$_{30}$ (Cy5 lactosome) were incorporated into cells, respectively.

FIG. 7 shows the measurement results of fluorescence spectra obtained in Example 5-4, when an antibody-modified lactosome encapsulating 20 mol % of IC71-PLLA$_{30}$ (anti HER2 lactosome) and an antibody-unmodified lactosome encapsulating 20 mol % of IC71-PLLA$_{30}$ (lactosome) were brought into contact with or incorporated into cells (N87, BT-474, SK-BR-3, and MCF-7), respectively.

FIG. 8 shows the results of fluorescence imaging of a tumor-bearing mouse using anti HER2 scFv-lactosome (A) encapsulating 1 mol % of IC71-PLLA$_{30}$, and a tumor-bearing mouse using anti HER2 scFv-lactosome (B) encapsulating 20 mol % of IC71-PLLA$_{30}$, obtained in Example 6.

FIG. 9 shows temporal changes in the fluorescence intensities of a tumor site (A) and a background (B) based on the results of fluorescence imaging, obtained in Example 6.

FIG. 10 shows temporal changes in the fluorescence intensity ratio between the tumor site and the background based on the results of fluorescence imaging, obtained in Example 6.

MODES FOR CARRYING OUT THE INVENTION

[1. Amphiphilic Block Polymer]

Figure 1:
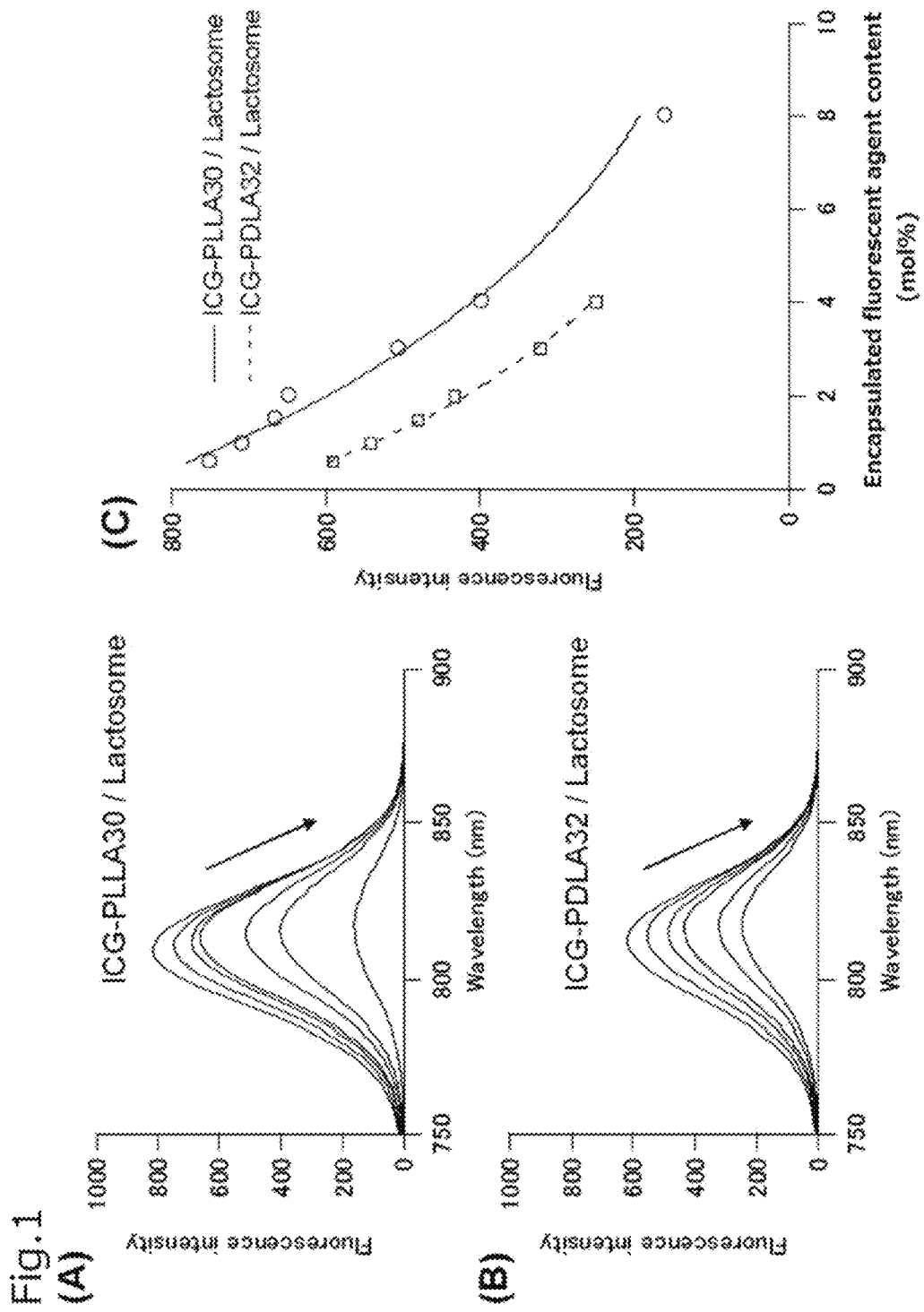
Figure 2:
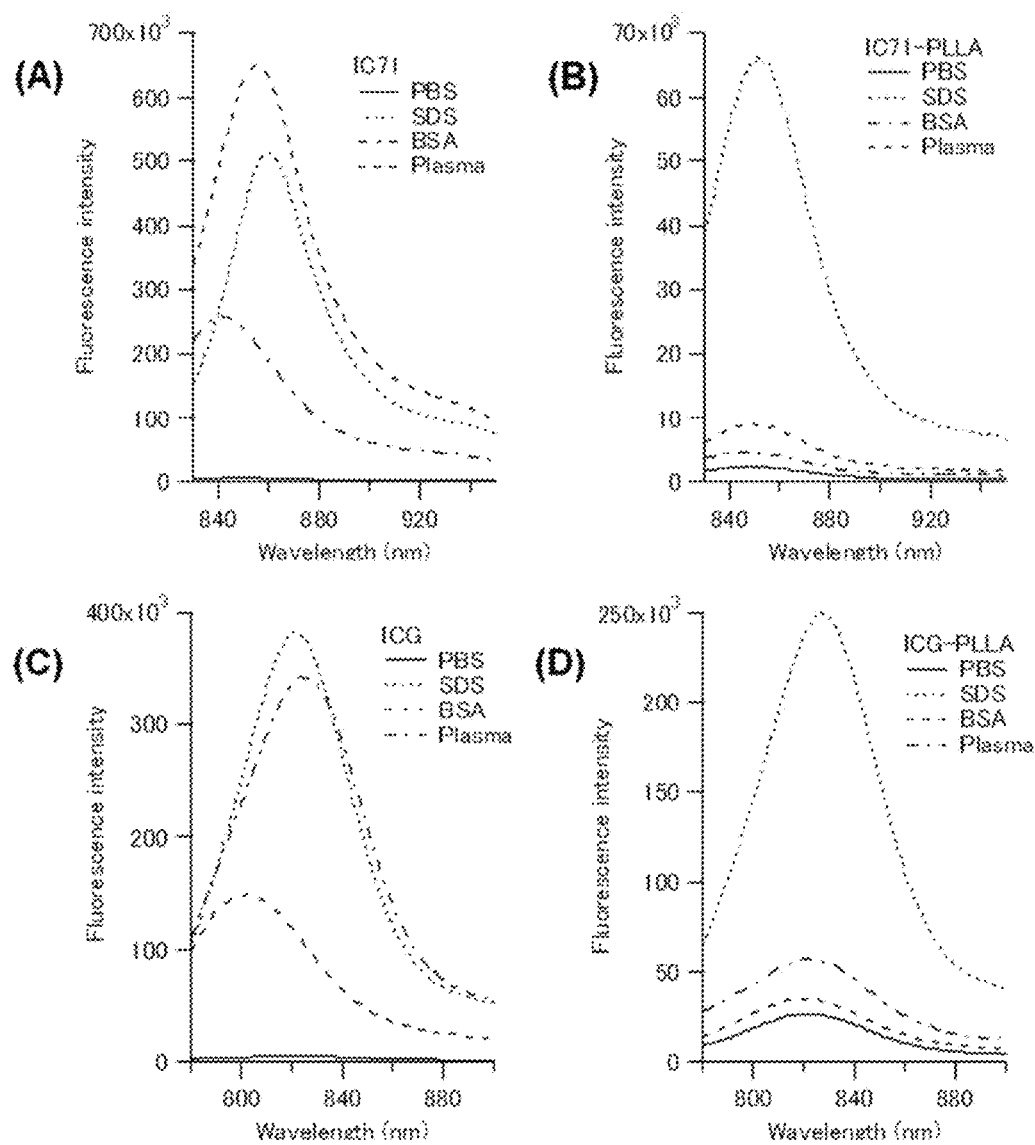
FIG. 2 shows the measurement results of fluorescence spectra obtained in Example 3, when PBS, SDS, BSA, or plasma was added to lactosomes each encapsulating 20 mol % of IC7-1, IC71-PLLA, ICG, or ICG-PLLA.

An amphiphilic block polymer in the present invention has the following hydrophilic block and hydrophobic block. Hereinbelow, in the present invention, the term "amino acid" is used as a concept including natural amino acids, unnatural amino acids, and derivatives thereof by modification and/or chemical alteration. Further, in the specification, amino acids include α-, β-, and γ-amino acids. Among them, α-amino acids are preferred.

[1-1. Hydrophilic Block Chain]

In the present invention, the specific degree of the physical property "hydrophilicity" of a hydrophilic block chain is not particularly limited, but, at least, the hydrophilic block chain shall be hydrophilic enough to be a region relatively more hydrophilic than a specific hydrophobic block chain that will be described later so that a copolymer composed of the hydrophilic block chain and the hydrophobic block chain can have amphiphilicity as a whole molecule of the copolymer, or so that the amphiphilic block polymer can self-assemble in a solvent to form a self-assembly, preferably a particulate self-assembly.

The hydrophilic block chain is a hydrophilic molecular chain comprising, as an essential hydrophilic structural unit, a unit selected from the group consisting of a sarcosine-derived unit and an alkylene oxide- or alkylene glycol-derived unit, and having the 20 or more essential hydrophilic structural units. More specifically, the hydrophilic molecular chains include: a hydrophilic polypeptide chain having 20 or more, preferably 30 or more sarcosine units; a hydrophilic polyether chain having 20 or more alkylene oxide units; and a hydrophilic complex chain having a total of 20 or more, preferably 30 or more units of both a sarcosine unit and an alkylene oxide unit.

Sarcosine is N-methylglycine.

Specific examples of the alkylene oxide unit include an ethylene oxide unit (polyethylene glycol unit), a propylene oxide unit (propylene glycol), and the like. In the alkylene oxide unit, hydrogen may be substituted.

When the hydrophilic block chain has a structural unit other than the sarcosine unit and the alkylene oxide unit, such a structural unit is not particularly limited and examples thereof include amino acids other than sarcosine (including hydrophilic amino acids and other amino acids). Such amino acids are preferably α-amino acids. Examples of the α-amino acids include serine, threonine, lysine, aspartic acid, and glutamic acid.

In the hydrophilic block chain, the kind and ratio of the structural unit constituting the hydrophilic block chain are appropriately determined by those skilled in the art so that the block chain can have such hydrophilicity as described above as a whole.

The hydrophilic block chain can be designed so that the upper limit of the number of structural units is, for example, about 500. In the present invention, a hydrophilic block chain whose number of structural units is about 30 to 300, preferably about 50 to 200 may be often synthesized. If the number of structural units exceeds about 500, when a molecular assembly is formed, the resultant molecular assembly tends to be poor in stability. If the number of structural units is less than 30, formation of a molecular assembly tends to be difficult per se.

In the hydrophilic block chain, all the same structural units may be continuous or discontinuous. When the hydrophilic block chain contains another structural unit other than the above-described specific units, the kind and ratio of the another structural unit are appropriately determined by those skilled in the art so that the block chain can have the above-described hydrophilicity as a whole. In this case, molecular design is preferably performed so that basic characteristics that will be described later are not impaired.

Sarcosine (i.e., N-methylglycine) is highly water-soluble, and a sarcosine polymer has an N-substituted amide and therefore can be cis-trans isomerized as compared to a normal amide group, and has high flexibility due to less steric hindrance around the C$^\alpha$ carbon atom. The use of such a polypeptide as a structural block chain is very useful in that the block chain can have, as basic characteristics, both high hydrophilicity and high flexibility.

Further, a polyalkylene oxide chain is highly hydrophilic and has no adverse effects such as immunogenicity and toxicity. The use of such a polyether chain as a structural block chain is very useful in that the block chain can have, as basic characteristics, high hydrophilicity and the ability to reduce the antigenicity of a carrier agent and impart the carrier agent excellent stability and retainability in the blood.

[1-2. Hydrophobic Block Chain]

In the present invention, the specific degree of the physical property "hydrophobicity" of a hydrophobic block chain is not particularly limited, but, at least, the hydrophobic block chain shall be hydrophobic enough to be a region relatively more hydrophobic than the specific hydrophilic block chain so that a copolymer composed of the hydrophobic block chain and the hydrophilic block chain can have amphiphilicity as a whole molecule of the copolymer, or so that the amphiphilic block polymer can self-assemble in a solvent to form a self-assembly, preferably a particulate self-assembly.

The hydrophobic block chain is a hydrophobic molecular chain comprising, as an essential structural unit, a unit selected from the group consisting of an amino acid-derived structural unit and a hydroxylic acid-derived structural unit, and having the 20 or more essential structural units. More specifically, the hydrophobic molecular chains include: a hydrophobic polypeptide chain having 20 or more hydrophobic amino acid units; a hydrophobic polyester chain having 20 or more hydroxylic acid units; and a hydrophobic depsipeptide chain having a total of 20 or more units of both an amino acid unit and a hydroxylic acid unit.

The hydrophobic block chain in the present invention preferably has a helix structure.

Most of the hydrophobic amino acids have an aliphatic side chain, an aromatic side chain, and the like. Examples of natural amino acids include glycine, alanine, valine, leucine, isoleucine, proline, methionine, tyrosine, and tryptophan. Examples of unnatural amino acids include, but are not limited to, amino acid derivatives such as glutamic acid methyl ester, glutamic acid benzyl ester, aspartic acid methyl ester, aspartic acid ethyl ester, aspartic acid benzyl ester, and the like.

Examples of the hydroxylic acid include, but are not limited to, glycolic acid, lactic acid, hydroxyisobutyric acid, and the like.

In the hydrophobic block chain, the kind and ratio of the structural unit constituting the hydrophobic block chain are appropriately determined by those skilled in the art so that the block chain becomes hydrophobic as a whole.

The hydrophobic block chain can be designed so that the upper limit of the number of structural units is, for example, about 100. In the present invention, a hydrophobic block chain whose number of structural units is about 10 to 80, preferably about 20 to 50 may be often synthesized. If the number of structural units exceeds about 100, when a molecular assembly is formed, the resultant molecular assembly tends to be poor in stability. If the number of structural units is less than 10, formation of a molecular assembly tends to be difficult per se.

In the hydrophobic block chain, all the same structural units may be continuous or discontinuous. When the hydrophobic block chain contains another structural unit other than the above-described specific units, the kind and ratio of the another structural unit are appropriately determined by those skilled in the art so that the block chain can have the above-described hydrophobicity as a whole. In this case, molecular design is preferably performed so that basic characteristics that will be described later are not impaired.

The amino acid unit and the hydroxylic acid unit used in the hydrophobic block chain have excellent biocompatibility and stability. Therefore, a molecular assembly obtained from the amphiphilic substance having such polylactic acid as a structural block is very useful from the viewpoint of applicability to a living body, especially a human body.

Further, in particular, polylactic acid is rapidly metabolized due to its excellent biodegradability, and is therefore less likely to accumulate in tissue other than cancer tissue in a living body. Therefore, a molecular assembly obtained from the amphiphilic substance having such polylactic acid as a structural block is very useful from the viewpoint of specific accumulation in cancer tissue.

And, further, polylactic acid has excellent solubility in a low boiling point solvent, and therefore the use of a hazardous high boiling point solvent can be avoided when a molecular assembly is obtained from the amphiphilic substance having such polylactic acid as a structural block. Therefore, such a molecular assembly is very useful from the viewpoint of safety for a living body.

Furthermore, adjustment of the chain length of polylactic acid is preferred, in that the adjustment contributes, as one factor, to the control of the shape and size of a molecular assembly obtained from the amphiphilic substance having such polylactic acid as a structural unit. Therefore, the use of such a structural block is very useful from the viewpoint of the versatility of shapes of a resultant molecular assembly.

From the viewpoint of optical purity, the hydrophobic block chain may include the following variations.

For example, the lactic acid units constituting the hydrophobic block chain may include only L-lactic acid units, or may include only D-lactic acid units, or may include both L-lactic acid units and D-lactic acid units. The hydrophobic block chain may be used singly or in combination of two or more of them selected from the above examples.

In a case where the lactic acid units include both L-lactic acid units and D-lactic acid units, the order of polymerization of L-lactic acid units and D-lactic acid units is not particularly limited. For example, L-lactic acid units and D-lactic acid units may be polymerized so that one or two L-lactic acid units and one or two D-lactic acid units are alternately arranged, or may be randomly polymerized, or may be block-polymerized.

Therefore, in a case where the lactic acid units include both L-lactic acid units and D-lactic acid units, the amount of each of the lactic acid units is not particularly limited. That is, the amount of L-lactic acid units contained in the hydrophobic block chain and the amount of D-lactic acid units contained in the hydrophobic block chain may be different from each other, or may be the same, and in this case the 10 or more lactic acid units may be a racemate having an optical purity of 0% as a whole.

[1-3. Other Groups]

In the present invention, the structural units constituting the amphiphilic block polymer may have another group. Examples of such a group include functional groups that allow the nanoparticle according to the present invention to have a form, a function and the like so that the nanoparticle becomes more useful as a molecular probe for, for example, a molecular imaging system or a drug delivery system. The functional group is, for example, an organic group, and is appropriately selected by those skilled in the art. Examples of the functional group include a functional group that improves the stability of the nanoparticle in blood, and a functional group that can bind to a biomolecule expressed in a target cell to control the directivity of the nanoparticle thereby improving the targeting capability of the nanoparticle.

Examples of a water-soluble polymer include polymers such as a polyether chain, a polyvinyl alcohol chain, and the like. Examples of a sugar chain include stabilizing agents such as carboxymethyl cellulose, amylose, and the like; and a sugar chain having the ability to specifically bind to a protein expressed in a cell in a target site.

Examples of an antibody include those having the ability to specifically bind to an antigen expressed in a cell in a target site.

Examples of a ligand include adhesion factors such as RGD (arginine-glycine-aspartic acid) and the like.

Such a group can bind to a terminal structural unit in the hydrophilic block of the amphiphilic block polymer. This makes it possible, when a nanoparticle is formed as a micelle, for the nanoparticle to be in the form of retaining the functional group on a surface of the nanoparticle, that is, to be in the form of surface-modified with the functional group.

[2. Fluorescent Dye]

In the present invention, a fluorescent dye encapsulated in a carrier agent is a polylactic acid-bound cyanine compound comprising at least a fluorescent group and a polylactic acid group.

[2-1. Fluorescent Group]

The fluorescent group in the fluorescent dye is represented by the following general formula (I).

[Chemical formula 12]

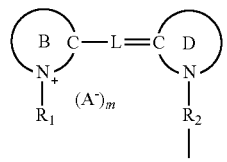

(I)

In the formula (I), $R_1$ is a hydrocarbon group which may be substituted, and $R_2$ is a bivalent hydrocarbon group which may be substituted.

The hydrocarbon group as $R_1$ may be an alkyl group having 1 to 20 carbon atoms, preferably 2 to 5 carbon atoms.

The hydrocarbon group as $R_2$ may be an alkylene group having 1 to 20 carbon atoms, preferably 2 to 5 carbon atoms.

A substituent group in each of $R_1$ and $R_2$ may be an anionic substituent group; and may be a carboxyl group, a carboxylate group, a metal carboxylate group, a sulfonyl group, a sulfonate group, a metal sulfonate group, or a hydroxyl group. The metal may be an alkali metal or an alkaline earth metal.

L is a linking group that constitutes a polymethine chain, and may include a ring structure and may be substituted. The length of the polymethine chain may be, for example, from 3 to 7 carbon atoms. Preferred examples of the linking group L constituting a polymethine chain include those having the following structures.

[Chemical formula 13]

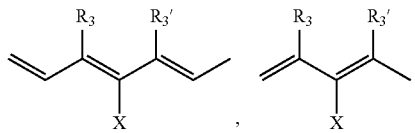

In the above formula, $R_3$ and $R_3'$ are hydrogen or are linked together to form a ring structure. The ring structure has at least one unsaturated bond such as an ethylenic double bond, and the unsaturated bond electronically resonates as a part of the polymethine chain, and examples of the ring structure include a cyclopentene ring, a cyclohexene ring, and the like. $R_3$ and $R_3'$ may be linked together to form a ring structure, thereby to make the molecular structure of the fluorescent dye rigid.

X is hydrogen or a halogen. The halogen may be Cl, Br, or I.

$A^-$ is an anion and m is 0 or 1. When m is 0, any one of $R_1$ and $R_2$ and below-mentioned $R_4$ and $R_5$ is an anionic group so that a molecule has a betaine structure as a whole. When m is 1, $A^-$ may be a halogen ion such as $Cl^-$, $Br^-$, or $I^-$; $ClO_4^-$, $BF_4^-$, $PF_6^-$, $SbF_6^-$, $SCN^-$, or the like.

The ring B and the ring D may be the same or different from each other and each is a nitrogen-containing heterocycle. The ring B and the ring D are preferably each a nitrogen-containing condensed aromatic heterocycle. For example, the ring B and the ring D may be each a nitrogen-containing bicyclic or tricyclic aromatic heterocycle. The ring B and the ring D are preferably the same.

Preferred examples of the ring B include the following structures.

[Chemical formula 14]

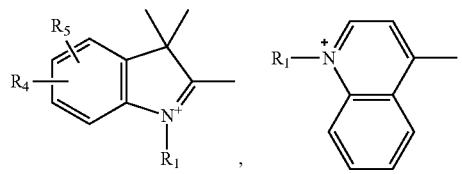

Preferred examples of the ring D include the following structures.

[Chemical formula 15]

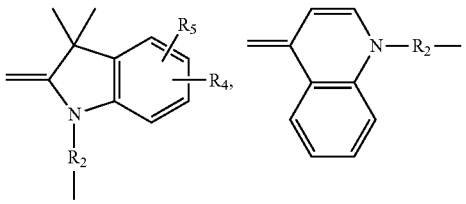

In the above formulas, $R_4$ and $R_5$ may be each hydrogen or an anionic substituent group. The anionic substituent group may be a carboxylate group, a metal carboxylate group, a sulfonate group, or a metal sulfonate group. The metal may be an alkali metal or an alkaline earth metal.

Alternatively, $R_4$ and $R_5$ may be linked together to form an aryl ring. The aryl ring may be a benzene ring which may be substituted.

In the present invention, preferred examples of the fluorescent group include a group derived from an indocyanine compound represented by the following structural formula (II).

[Chemical formula 16]

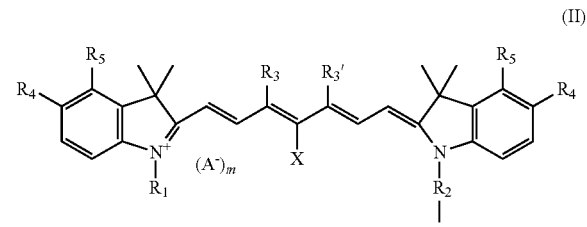

(II)

Specific examples of the fluorescent group represented by the structural formula (II) include: an IC7-1 group (III), an ICG group (IV), and an IR820 group (V) whose ring B and ring D are both nitrogen-containing tricyclic aromatic heterocycles; an IR783 group (VI) and an IR806 group (VII) whose ring B and ring D are both nitrogen-containing bicyclic aromatic heterocycles; and an IC7-2 group (VIII) whose ring B is a nitrogen-containing tricyclic aromatic heterocycle and ring D is a nitrogen-containing bicyclic aromatic heterocycle. The structural formulas of these groups are shown below.

[Chemical formula 17]

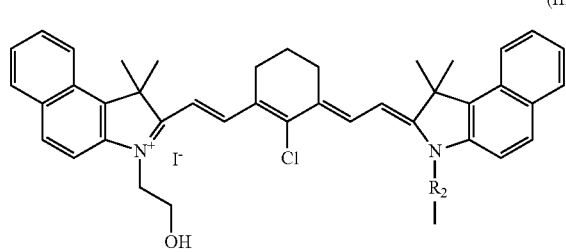
(III)

[Chemical formula 18]

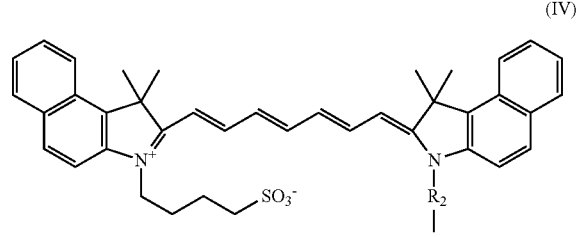
(IV)

[Chemical formula 19]

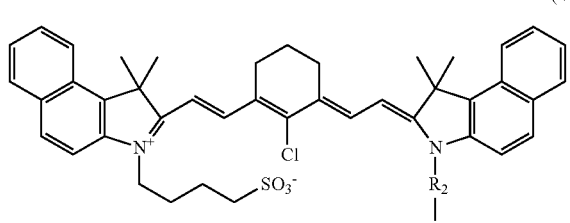
(V)

[Chemical formula 20]

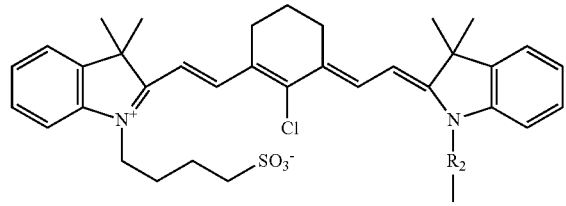
(VI)

[Chemical formula 21]

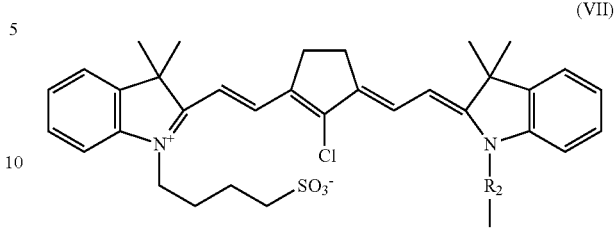
(VII)

[Chemical formula 22]

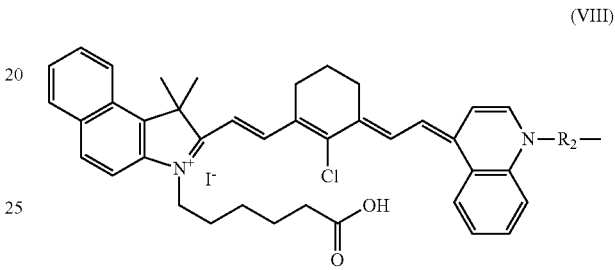
(VIII)

The cyanine-based fluorescent groups represented by the above formulas (II) to (VIII) emit near-infrared light. In the near-infrared region (700 to 1,300 nm), absorption by each substituent group having a hydrogen bond occurs, but the degree of the absorption is relatively low. For this reason, near-infrared light has the property of easily penetrating living tissue. The utilization of such a property of near-infrared light makes it possible to obtain information inside a body without placing an unnecessary burden on the body.

In the present invention, other preferred examples of the fluorescent group include a group derived from an indocyanine compound represented by the following structural formula (IX).

[Chemical formula 23]

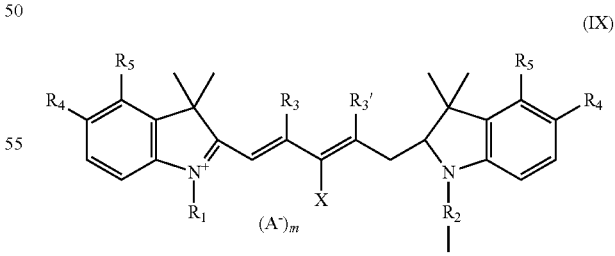
(IX)

Specific examples of the fluorescent group represented by the structural formula (IX) include a group derived from Cy5 and a group derived from Cy7. More specific examples of the group derived from Cy5 include a group represented by the following structural formula (X).

[Chemical formula 24]

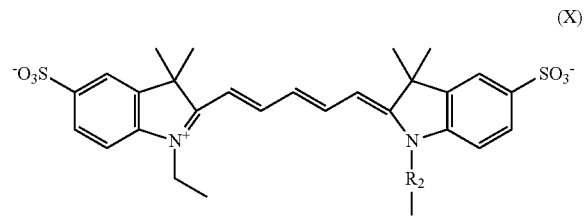

(X)

The fluorescent group whose polymethine bridge has less carbon atoms than those of the above fluorescent groups (II) to (VIII), such as the cyanine-based fluorescent group exemplified by the formula (IX) or (X), emits light having a shorter wavelength than light emitted by the fluorescent groups (II) to (VIII), and is therefore useful for obtaining, when a surgical operation is required, information about the size and position of tissue to be removed after laparotomy or thoracotomy, rather than for non-invasively obtaining information inside a body.

[2-2. Polylactic Acid Group]

The polylactic acid group is a group whose main structural component is a lactic acid unit. All the lactic acid units may be either continuous or discontinuous. Basically, the structure or chain length of the polylactic acid group can be determined based on the same viewpoint as in the molecular design of the hydrophobic block chain described above in 1-2. This also makes it possible to obtain the effect that affinity between the fluorescent dye (polylactic acid-bound cyanine compound) and the hydrophobic block chain of the amphiphilic block polymer in a molecular assembly is excellent.

The number of lactic acid units of the polylactic acid group is 5 to 50, preferably 15 to 35. The polylactic acid-bound cyanine compound is molecularly designed within the above range so that the entire length of the polylactic acid-bound cyanine compound does not exceed the length of the above-described amphiphilic block polymer. Preferably, the polylactic acid-bound cyanine compound is molecularly designed so that its entire length does not exceed a length of twice the length of the hydrophobic block in the amphiphilic block polymer. If the number of structural units exceeds the above range, when a molecular assembly is formed, the resulting molecular assembly tends to be poor in stability. If the number of structural units is less than the above range, a nanoparticle tends to be difficult to maintain an off-state in a blood component.

From the viewpoint of optical purity, the polylactic acid group may include the following variations.

For example, the lactic acid units constituting the polylactic acid group may include only L-lactic acid units, or may include only D-lactic acid units, or may include both L-lactic acid units and D-lactic acid units. The polylactic acid group may be used singly or in combination of two or more of them selected from the above examples.

In a case where the lactic acid units include both L-lactic acid units and D-lactic acid units, the order of polymerization of L-lactic acid units and D-lactic acid units is not particularly limited. For example, L-lactic acid units and D-lactic acid units may be polymerized so that one or two L-lactic acid units and one or two D-lactic acid units are alternately arranged, or may be randomly polymerized, or may be block-polymerized.

Therefore, in a case where the lactic acid units include both L-lactic acid units and D-lactic acid units, the amount of each of the lactic acid units is not particularly limited. That is, the amount of L-lactic acid units contained in the hydrophobic block chain and the amount of D-lactic acid units contained in the hydrophobic block chain may be different from each other, or may be the same, and in this case the 10 or more lactic acid units may be a racemate having an optical purity of 0% as a whole.

[2-3. Specific Examples of Polylactic Acid-Bound Cyanine Compound]

In the polylactic acid-bound cyanine compound, the fluorescent group may bind to the terminal lactic acid unit of the polylactic acid group. The polylactic acid-bound cyanine compound may further have any structural component which is chemically or biochemically acceptable other than fluorescent group and lactic acid units in molecular design. In this case, the other structural components are contained to the extent that the "hydrophobicity" of the polylactic acid-bound cyanine compound as a whole does not depart from the above definition.

Specific examples of the polylactic acid-bound cyanine compound (III-i), (VI-i), and (X-i) are shown below. In the following formulas, n is an integer of 5 to 50. The compound (III-i) has an IC7-1 group as the fluorescent group. Further, the compound (VI-i) has an ICG group as the fluorescent group. Further, the compound (X-i) has a Cy5 group as the fluorescent group. In the present description, when the polylactic acid-bound cyanine compound has an n of, for example, 30, the compound is described as, for example, IC71-PLLA$_{30}$, IC71-PDLA$_{30}$, ICG-PLLA$_{30}$, ICG-PDLA$_{30}$, Cy5-PLLA$_{30}$, Cy5-PDLA$_{30}$, or the like.

Similarly, even when the fluorescent group has other structures, the structure of the polylactic acid-bound cyanine compound can be determined by those skilled in the art.

[Chemical formula 25]

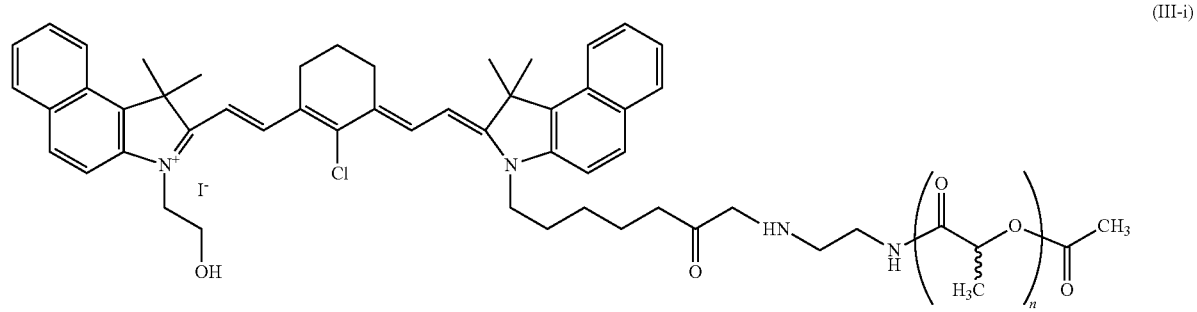

(III-i)

[Chemical formula 26]

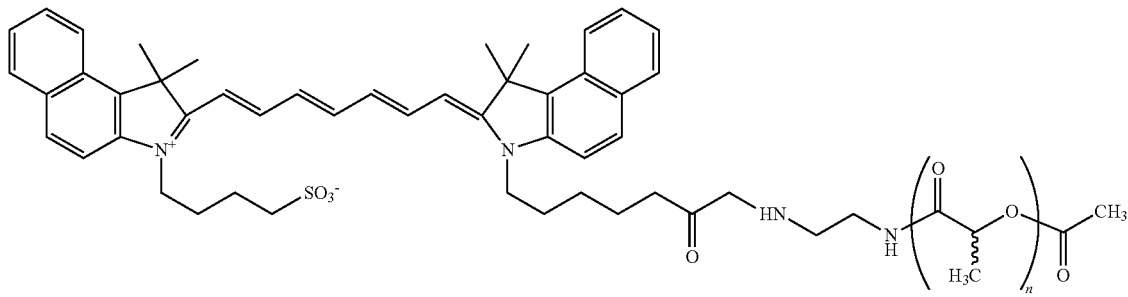

(IV-i)

[Chemical formula 27]

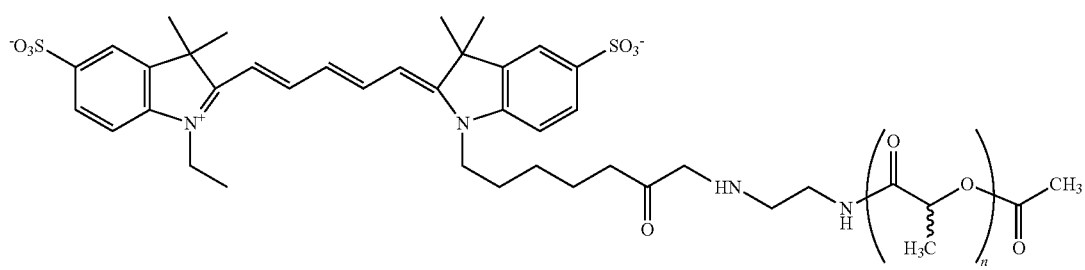

(X-i)

[3. Nanoparticle]

A nanoparticle according to the present invention is a structure in which the above-described fluorescent dye is encapsulated in a molecular assembly, as a carrier agent, that is formed by aggregation or self-assembling orientational association of the above-mentioned amphiphilic block polymer.

[3-1. Structure of Nanoparticle]

The molecular assembly in the present invention forms a micelle. The amphiphilic block polymer self-assembles so that a hydrophobic block chain forms a core portion. On the other hand, the fluorescent dye is located in the hydrophobic core portion. At this time, the fluorescent dye that is a cyanine-based fluorescent group is associated. Therefore, fluorescence is quenched (i.e., in an off-state that will be described later).

The molecular assembly that is a carrier agent of the nanoparticle according to the present invention can achieve, in an on-state that will be described later, both flexibility that allows the nanoparticle to respond to its external environment and encapsulation stability that allows the fluorescent dye to be held by the molecular assembly.

[3-2. Amount of Fluorescent Dye Encapsulated in Nanoparticle]

The nanoparticle according to the present invention encapsulates two or more molecules of the fluorescent dye per single nanoparticle. For example, the amount of the fluorescent dye may be 1 to 50 mol % with respect to the total amount of the amphiphilic block polymer and the fluorescent dye. Preferably, the amount of the fluorescent dye may be 5 to 20 mol %, or 10 to 20 mol %. In the present invention, 1 mol % of the fluorescent dye with respect to the total amount of the amphiphilic block polymer and the fluorescent dye generally corresponds to two molecules of the fluorescent dye encapsulated in the single nanoparticle. If the amount of the fluorescent dye is less than the above range, the nanoparticle tends to be unable to have a switching function, and if the amount of the fluorescent dye exceeds the above range, formation of the nanoparticle tends to be difficult.

Further, encapsulation of the fluorescent dye has the effect of increasing the volume of the hydrophobic core portion of the nanoparticle, and therefore there is a case where the particle size of the nanoparticle is controlled by adjusting the amount of the fluorescent dye encapsulated in the nanoparticle.

[3-3. Switching Function of Nanoparticle]

[3-3-1. Off Function]

The nanoparticle according to the present invention encapsulates two or more molecules of the fluorescent dye. The encapsulated two or more molecules of the fluorescent dye are self-quenched by their association.

The degree of quenching depends on the amount of the encapsulated fluorescent dye. That is, the intensity of fluorescence per certain amount of the fluorescent dye exponentially reduces as the amount of the encapsulated fluorescent dye increases. The degree of the reduction may vary depending on the kind of fluorescent dye. When the intensity of fluorescence is measured at a certain fluorescent dye concentration (e.g., 0.48 µM), there is a case where the intensity of fluorescence is reduced to ½ every time the amount of the encapsulated fluorescent dye increases by 2.8 to 3.7 mol %. An example of the case where the intensity of fluorescence may be reduced to ½ every time the amount of the encapsulated fluorescent dye increases by 2.8 mol % is a case where the intensity of fluorescence is measured when the concentration of lactosomes (molecular assemblies composed of a polysarcosine-polylactic acid amphiphilic block polymer and functioning as carrier parts of the nanoparticles) encapsulating poly(D)lactic acid-bound ICG is adjusted to the above concentration. Further, an example of the case where the intensity of fluorescence may be reduced to ½ every time the amount of the encapsulated fluorescent dye increases by 3.7 mol % is a case where the intensity of fluorescence is measured when the concentration of lactosomes encapsulating poly(L)lactic acid-bound ICG is adjusted to the above concentration.

Therefore, the nanoparticle according to the present invention can be efficiently quenched even when the number of fluorescent molecules is small.

The quenching state (off-state) as described above is maintained in at least an environment during nanoparticle preparation and an environment in which a blood component is present. The environment in which the off-state is maintained may be any environment as long as an on-state that will be described later is not caused. Examples of such an environment include a water-based environment such as water or an aqueous solution containing no surfactant; an anhydrous environment; and an environment in which a blood component is present. The water or aqueous solution may be any water or aqueous solution as long as it is biochemically or pharmaceutically acceptable, and specific examples thereof include distilled water for injection, normal saline, a buffer solution, and the like. A preferred example thereof includes phosphate buffered saline. The nanoparticle in an anhydrous environment refers to a freeze-dried nanoparticle. Examples of the blood component include blood, plasma, serum, albumin, and the like. The nanoparticle in the environment in which a blood component is present refers to, for example, a nanoparticle that has been administered into a blood vessel but has not yet reached (i.e., has not yet come into contact with) a cell in a target site.

[3-3-2 On Function]

The nanoparticle in the above-described off-state responds to a change in its outer environment and is put into a state where the nanoparticle recovers fluorescence (i.e., an on-state).

An environment causing the on-state is not particularly limited as long as the fluorescent dye encapsulated in the nanoparticle can be dissociated. Such an environment where the fluorescent dye can be dissociated is considered as an environment having the effect of deforming the structure of the molecular assembly as a carrier agent.

A specific example of a component contained in the environment causing the on-state includes a cell component. That is, the on-state is caused by contact with or incorporation into a cell. The cell is not particularly limited. From the viewpoint of utilizing the EPR effect through the nanoparticle according to the present invention, more specific examples of the cell include cells present in vascular lesion sites (e.g., a malignant tumor site, an inflamed site, an arterial sclerosis site, an angiogenesis site, etc.). As specific examples of the cell component, components constituting cells may be mentioned, but secretions from cells, cell tissue fluids, and the like that can be transferred between different cells are excluded. Specific examples of the cell component include: intracellular enzymes having the action of deforming or decomposing the structure of the molecular assembly used in the present invention as a carrier agent, such as enzymes (e.g., protease, esterase, and sarcosine dehydrogenase), lysosome-degrading enzyme, and the like; and intracellular components that can dissociate the fluorescent dye encapsulated in the molecular assembly, such as proteins (e.g., albumin), lipids, and the like. One example of a mechanism for causing the on-state is considered as follows: the structure of the molecular assembly as a carrier agent is decomposed by an intracellular enzyme such as lysosome-degrading enzyme, and then the liberated dye adsorbs to a nearby protein or a lipid membrane so that the on-state is caused.

The cell component can put the nanoparticle into the on-state as long as a concentration of the cell component is at least a level in an in vivo environment. The concentration of the cell component at which the on-state can be caused is in the range of, for example, 0.03 to 10 wt %, or 0.4 to 47 times the concentration of the encapsulated fluorescent dye (molar basis), which is merely one example. The above range is applied to a case where the cell component is, for example, albumin. When the concentration is less than the above range, the intensity of fluorescence does not tend to be sufficiently recovered. The concentration may exceed the above range, but when it exceeds the above range, the intensity of fluorescence tends to hit a peak due to maximum fluorescence recovery.

When being put into the on-state, the nanoparticle recovers fluorescence that has been quenched during the off-state. The intensity of fluorescence after recovery may vary depending on the kind of carrier agent or encapsulated fluorescent dye, but may be larger than fluorescence intensity during the off-state (e.g., during a state in which the nanoparticle is present in phosphate buffered saline or in a blood component). Although the following is merely one example, when the amount of the encapsulated fluorescent dye is 1 to 50 mol % (corresponding to 2 to 200 molecules of the fluorescent dye per single nanoparticle), the intensity of fluorescence may be about 1.1 to 12,000 times higher at the maximum; or when the amount of the encapsulated fluorescent dye is 10 to 20 mol % (corresponding to 22 to 50 molecules of the fluorescent dye per single nanoparticle), the intensity of fluorescence may be about 11 to 130 times higher at the maximum. In the present invention, the intensity of fluorescence after recovery is preferably 10 times or more higher than fluorescence intensity during the off-state. More preferably, the intensity of fluorescence after recovery is 100 times or more higher. The upper limit of the above range is not particularly limited, but is, for example, 20,000 times or 15,000 times.

[3-4. Size of Nanoparticle]

[3-4-1. Size of Nanoparticle]

For example, the nanoparticle according to the present invention has a particle size of 10 to 500 nm. Here, the "particle size" refers to a particle diameter that appears at the highest frequency in a particle size distribution, that is, a median particle diameter. When the particle size is smaller than 10 nm, it is difficult to form the nanoparticle. On the other hand, when the particle size exceeds 500 nm, there is a case where, particularly when administered to a living body by injection, the nanoparticles are not suitable for use in an injection.

[3-4-2. Measurement of Nanoparticle Size]

A method for measuring the size of the nanoparticle according to the present invention is not particularly limited, and is appropriately selected by those skilled in the art. Examples of such a method include an observation method using a transmission electron microscope (TEM) and a dynamic light scattering (DLS) method. In the DLS method, the translational diffusion coefficient of a particle undergoing Brownian movement in a solution is measured.

[3-4-3. Control of Nanoparticle Size]

An example of a means for controlling the size of the molecular assembly includes the control of chain length of the amphiphilic block polymer. Preferably, adjustment of the degree of polymerization of the hydrophobic block in the amphiphilic block polymer is effective. Another example of the means for controlling the size of the molecular assembly includes the control of the amount of the fluorescent compound to be encapsulated.

[3-5. Formation of Nanoparticle]

A method for forming the nanoparticle is not particularly limited, and can be appropriately selected by those skilled in the art depending on the desired size and characteristics of the nanoparticle; the kind, properties and content of the fluorescent dye to be carried; or the like. If necessary, after nanoparticles are formed in the following manner, the obtained nanoparticles may be subjected to surface modification by a known method.

It is to be noted that the confirmation of formation of particles may be performed by electron microscope observation.

[3-5-1. Film Method]

A film method is a method that has been used for liposome preparation. The amphiphilic block polymer in the present invention has solubility in a low boiling point solvent, and therefore the nanoparticle can be prepared by this method.

The film method comprises the following steps of: preparing a solution, in a container (e.g., a glass container), containing the amphiphilic block polymer and the fluorescent dye in an organic solvent; removing the organic solvent from the solution to obtain, on an inner wall of the container, a film containing the amphiphilic block polymer and the fluorescent dye; and adding water or an aqueous solution to the container, and performing ultrasonic treatment or warming treatment to convert the film-shaped substance into molecular assemblies encapsulating the fluorescent dye to obtain a dispersion liquid of nanoparticles. Further, this film method may comprise the step of subjecting the dispersion liquid of nanoparticles to freeze-drying treatment.

The solution containing the amphiphilic block polymer and the fluorescent dye in an organic solvent may be prepared by previously preparing a film comprising the amphiphilic block polymer, and then adding a solution containing the fluorescent dye at the time of nanoparticle preparation to the film for dissolution.

The organic solvent to be used in the film method is preferably a low boiling point solvent. In the present invention, the low boiling point solvent refers to a solvent whose boiling point at 1 atmospheric pressure is 100° C. or lower, preferably 90° C. or lower. Specific examples of the low boiling point solvent include chloroform, diethyl ether, acetonitrile, ethanol, acetone, dichloromethane, tetrahydrofuran, hexane, and the like.

The use of such a low boiling point solvent to dissolve the amphiphilic block polymer and the fluorescent dye makes it very easy to perform solvent removal. A method for solvent removal is not particularly limited, and may be appropriately determined by those skilled in the art depending on the boiling point of an organic solvent to be used, or the like. For example, solvent removal may be performed under reduced pressure, or by natural drying.

After the organic solvent is removed, a film containing the amphiphilic block polymer and the fluorescent dye is formed on the inner wall of the container. Water or an aqueous solution is added to the container to which the film is attached. The water or aqueous solution is not particularly limited, and biochemically or pharmaceutically acceptable ones may be appropriately selected by those skilled in the art. Examples thereof include distilled water for injection, normal saline, and a buffer solution.

After water or an aqueous solution is added, warming treatment is performed. The film is peeled off from the inner wall of the container by warming, and in this process, molecular assemblies are formed. The warming treatment can be performed under the conditions of, for example, 70 to 100° C. and 5 to 60 minutes. After the completion of the warming treatment, a dispersion liquid in which molecular assemblies (nanoparticles) encapsulating the fluorescent dye are dispersed in the water or aqueous solution is prepared in the container.

The obtained dispersion liquid can be directly administered to a living body. That is, the nanoparticles do not need to be stored by themselves under solvent-free conditions.

On the other hand, the obtained dispersion liquid may be subjected to freeze-drying treatment. A method for freeze-drying treatment is not particularly limited, and any known method can be used. For example, the dispersion liquid of nanoparticles obtained in such a manner as described above may be frozen by liquid nitrogen, or the like, and sublimated under reduced pressure. In this way, a freeze-dried product of the nanoparticles is obtained. That is, the nanoparticles can be stored as a freeze-dried product. If necessary, water or an aqueous solution may be added to the freeze-dried product to obtain a dispersion liquid of nanoparticles, and the nanoparticles can be used. The water or aqueous solution is not particularly limited, and biochemically or pharmaceutically acceptable ones may be appropriately selected by those skilled in the art. Examples thereof include distilled water for injection, normal saline, and a buffer solution.

Here, the dispersion liquid before freeze-drying treatment may contain, in addition to the nanoparticles according to the present invention formed from the amphiphilic block polymer and the fluorescent dye, the amphiphilic block polymer and/or the fluorescent dye remaining per se without contributing to the formation of such nanoparticles. By subjecting such a dispersion liquid to freeze-drying treatment, in the process of concentration of a solvent, it is possible to further form nanoparticles from the amphiphilic block polymer and the fluorescent dye remaining without forming the nanoparticles according to the present invention. Therefore, preparation of the nanoparticles according to the present invention can be efficiently performed.

[3-5-2. Injection Method]

An injection method is a method used for preparation of not only the nanoparticle according to the present invention but also many other nanoparticles. In this method, an amphiphilic block polymer and a fluorescent dye are dissolved in an organic solvent such as trifluoroethanol, ethanol, hexafluoroisopropanol, dimethylsulfoxide, dimethylformamide, or the like to obtain a solution; and the solution is dispersed in a water-based solvent such as distilled water for injection, normal saline, or a buffer solution and subjected to purification treatment such as gel filtration chromatography, filtering, or ultracentrifugation; and then the organic solvent is removed to prepare nanoparticles. When nanoparticles obtained in this way using an organic solvent hazardous to a living body are administered to a living body, the organic solvent needs to be strictly removed.

[4. Fluorescent Molecular Imaging Method]

A fluorescent molecular imaging method according to the present invention comprises administering the above-described fluorescent nanoparticle to a living body as a probe. The fluorescent molecular imaging method according to the present invention is characterized by using the above-described fluorescent probe, and other specific procedures can be appropriately determined by those skilled in the art according to a known fluorescent molecular imaging method.

[4-1. Administration of Fluorescent Probe]

A living body to which the fluorescent probe is administered is not particularly limited, and may be a non-human animal. The non-human animal is not particularly limited, and may be a mammal other than a human. Specific examples thereof include primates, gnawing mammals (e.g., mice, rats), rabbits, dogs, cats, pigs, bovines, sheep, and horses.

A method for administration to a living body is not particularly limited, and can be appropriately determined by those skilled in the art. Therefore, the administration method may be either systemic or local as long as the fluorescent probe can come into contact with a cell component. That is, the administration of the molecular probe can be performed by any one of injection (needle injection or needleless injection), oral administration, and external application.

The fluorescent probe according to the present invention has a switching function. Therefore, fluorescence is quenched after preparation of the fluorescent probe and in contact with a blood component after administration to a living body, but the fluorescent probe emits fluorescence when brought into contact with or incorporated into a cell in a target site.

[4-2. Administration Target]

The nanoparticle used as a fluorescent probe in the method according to the present invention is excellent in specific accumulation in a vascular lesion site (e.g., a malignant tumor site, an inflammatory site, an arterial sclerosis site, an angiogenic site). The fluorescent probe according to the present invention accumulates in the tissue of such a site due to EPR (enhanced permeability and retention) effect, and therefore its accumulation does not depend on the kind of tissue of a vascular lesion site. The administration target of the fluorescent probe according to the present invention is preferably a cancer. Examples of the cancer as the administration target include a wide variety of cancers such as liver cancers, pancreas cancers, lung cancers, uterine cervical cancers, breast cancers, and colon cancers.

[4-3. Detection of Fluorescent Probe]

A molecular imaging system according to the present invention comprises the step of detecting fluorescence derived from an administered fluorescent probe. By detecting the administered fluorescent probe, it is possible to observe the states of an administration target (especially, the position and size of tissue such as a cancer) from outside the body.

As a detection method, any means that can visualize the administered fluorescent probe can be used. The detection means can be appropriately determined by those skilled in the art depending on the kind of fluorescent dye contained in the fluorescent probe.

For example, irradiation of a living body, to which the fluorescent probe has been administered, with excitation light makes it possible to detect fluorescence emitted from the fluorescent dye contained in the fluorescent probe in the body.

Parameters such as an excitation wavelength and a fluorescence wavelength to be detected can be appropriately determined by those skilled in the art depending on the kind of fluorescent dye contained in the fluorescent probe to be administered and the kind of administration target.

The time from administration to the start of detection can be appropriately determined by those skilled in the art depending on the kind of fluorescent dye contained in the fluorescent probe to be administered and the kind of administration target. For example, detection may be started after a lapse of 1 to 24 hours from administration. If the time is shorter than the above range, a detected signal is too strong and therefore it tends to be difficult to clearly distinguish an administration target from other sites (background). On the other hand, if the time is longer than the above range, the fluorescent probe tends to be excreted from the administration target.

From the viewpoint of accuracy, the fluorescent probe is preferably detected by measurement of a living body not from one direction but from two or more directions. More specifically, the measurement is preferably performed from at least three directions, more preferably at least five directions. When measurement is performed from five directions, a living body can be measured from, for example, both right and left abdomen sides, both right and left sides of the body, and the back side.

EXAMPLES

Hereinbelow, the present invention will be described in more detail with reference to examples.

In the examples, nanoparticles according to the present invention were prepared using a polysarcosine-polylactic acid amphiphilic block polymer (PSar-PLLA), or an antibody-modified polysarcosine-polylactic acid amphiphilic block polymer (anti HER2 scFv-PSar-PLLA) as a carrier agent, and fluorescent compound-labeled polylactic acid ICG-PLLA$_{30}$, ICG-PDLA$_{32}$, or IC71-PLLA$_{30}$ (polylactic acid-bound cyanine compound) as a fluorescent dye encapsulated in the carrier agent. However, the present invention is not limited to these examples.

Further, for comparison purposes, nanoparticles were prepared using the above-described polysarcosine-polylactic acid amphiphilic block polymer (PSar-PLLA), as a carrier agent and ICG (Sigma) or IC7-1 as a fluorescent dye encapsulated in the carrier agent.

Experimental Example 1: Synthesis of N-[5-Anilino-3-chloro-2,4-(propane-1,3-diyl)-2,4-pentadiene-1-ylidene]anilinium Chloride (Compound 1)

Anhydrous DMF (13 mL, 0.17 mol) was placed in a 100 mL three-necked flask and cooled to 0° C. Phosphorous oxychloride (11 mL, 0.12 mol) was dropped thereinto for 15 minutes. After stirring at 0° C. for 1 hour, cyclohexanone (5.5 mL, 0.053 mol) was added. After stirring at room temperature for 1 hour, heating to reflux was performed and stirring was further performed for 1 hour. After cooling to room temperature, 18 mL of a mixed solution of aniline/EtOH=1/1 (volume ratio) was added. After 30 minutes, 110 mL of a mixed solution of H$_2$O/HCl=10/1 (volume ratio) was added and allowed to stand at 5° C. overnight. A precipitate was collected by filtration and washed with THF and cold water to give crystals, and the resultant crystals were dried with P$_2$O$_5$ in a desiccator to obtain a compound 1 (Scheme 1). A yield of 53.6% (10.2 g) was achieved.

Scheme 1

[Chemical formula 28]

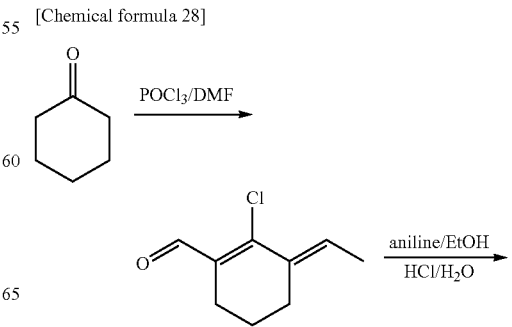

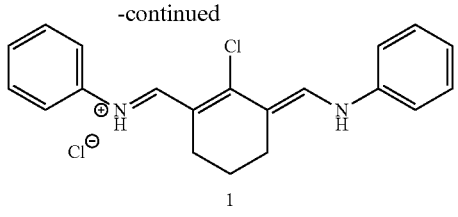

Experimental Example 2: Synthesis of 3-(5-Carboxy-pentyl)-1,1,2-trimethyl-1H-benzo[e]indolium; Iodide (Compound 2)

To a 50 mL eggplant flask, 6-Bromohexanoic Acid (8.4 g, 43.0 mmol), potassium iodide (7.2 g, 43 mmol), and 5 mL of toluene were added, and then 1,1,2-Trimethyl-1H-benzo[e]indole (3.0 g, 14.3 mmol) was added. After heating to reflux was performed for 15 hours, a precipitated solid was collected by filtration. The solid was washed with THF, cold water, and chloroform in this order, and dried in a desiccator to obtain a compound 2 (Scheme 2). A yield of 77% (5.0 g) was achieved.

Scheme 2

[Chemical formula 29]

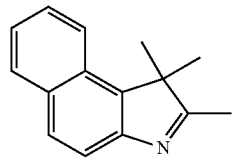

6-Bromohexanoic Acid
KI/Toluene
→

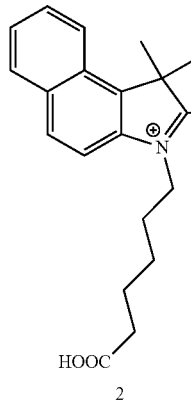

Experimental Example 3: Synthesis of Intermediate 3

The compound 1 (3.00 g, 8.35 mmol), the compound 2 (3.77 g, 8.35 mmol), and anhydrous sodium acetate (0.753 g, 9.19 mmol) were dissolved in 75.0 mL of anhydrous ethanol, and heated to reflux under a nitrogen atmosphere for 6 hours. After the completion of reaction, a 0.2 mol/L phosphate buffer solution (pH=7.0) was added for neutralization, and then an organic substance was extracted with chloroform. The extract was once concentrated, and then purified by column chromatography to obtain an intermediate 3 (Scheme 3). A yield of 25.5% (1.45 g) was achieved.

Scheme 3

[Chemical formula 30]

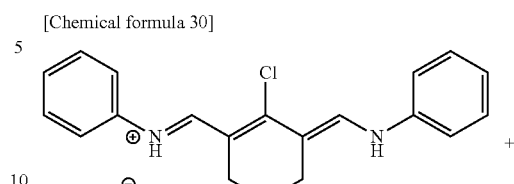

Experimental Example 4: Synthesis of 3-(2-Hydroxy-ethyl)-1,1,2-trimethyl-1H-benzo[e]indolium; Iodide (Compound 4)

To a 50 mL three-necked flask, 1,1,2-Trimethyl-1H-benzo[e]indole (2.0 g, 9.556 mmol) and 10 mL of anhydrous toluene were added, and heated to 80° C. under a nitrogen atmosphere. After the 1,1,2-Trimethyl-1H-benzo[e]indole was completely dissolved in the toluene, 2-Iodoethanol (1.64 g, 9.556 mmol) was added. After heating to reflux was performed for 2 hours, cooling to room temperature was performed and precipitated pale blue crystals were collected by filtration. The crystals were washed with toluene, and dried in a desiccator to obtain a compound 4 (Scheme 4). A yield of 33% (1.21 g) was achieved.

Scheme 4

[Chemical formula 31]

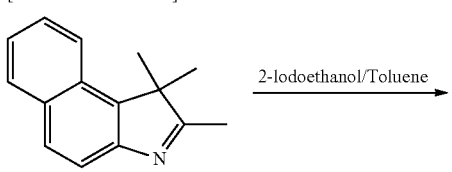

-continued

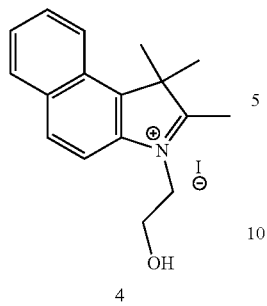

4

-continued

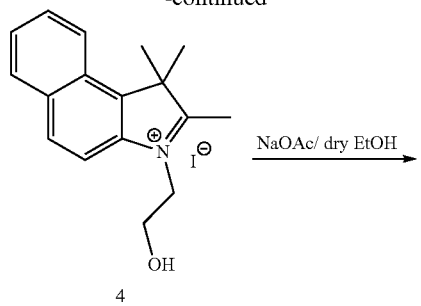

4    NaOAc/ dry EtOH →

Experimental Example 5: Synthesis of IC7-1

The intermediate 3 (1.16 g, 1.70 mmol), the compound 4 (0.714 g, 1.87 mmol), and anhydrous sodium acetate (0.153 g, 1.87 mmol) were dissolved in 29.0 mL of anhydrous ethanol, and heated to reflux under a nitrogen atmosphere for 5 hours. After the completion of reaction, a 0.2 mol/L phosphate buffer solution (pH=7.0) was added for neutralization, and then an organic substance was extracted with chloroform. The extract was once concentrated, and then purified by column chromatography to obtain IC7-1 (Scheme 5). A yield of 85.3% (1.22 g) was achieved.

Scheme 5

[Chemical formula 32]

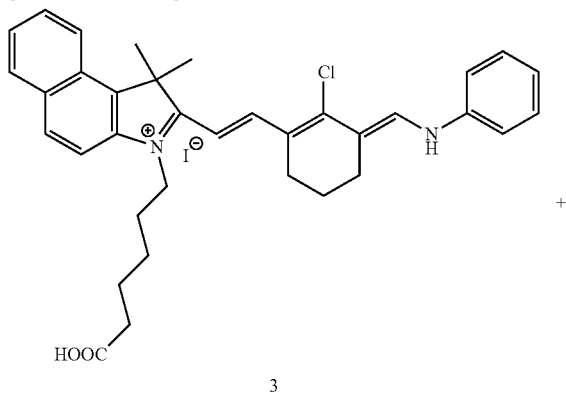

3

+

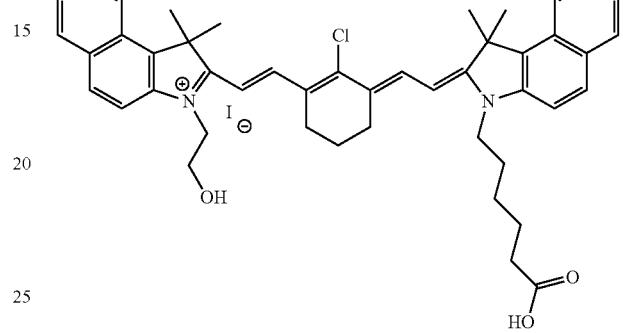

IC7-1

Experimental Example 6: Synthesis of IC7-1 NHS Ester

IC7-1 (600 mg, 0.713 mmol) was dissolved in 12 mL of anhydrous DMF, and the solution was cooled to 0 degree centigrade in an ice bath. Then, dicyclohexylcarbodiimide (DCC) (440 mg, 2.14 mmol) was added and the mixture was stirred for 20 minutes, and then N-hydroxysuccinimide (NHS) (246 mg, 2.14 mmol) was added and the mixture was returned to room temperature over 1.5 hours. Then, the mixture was stirred at room temperature for 2 days (Scheme 6). After the completion of the reaction, ethyl acetate was added to deposit DC urea, and the DC urea was filtered out. The filtrate was concentrated and purified by flash column chromatography to obtain target C7-1 NHS ester. A yield of 14.9% (100.0 mg) was achieved.

Scheme 6

[Chemical formula 33]

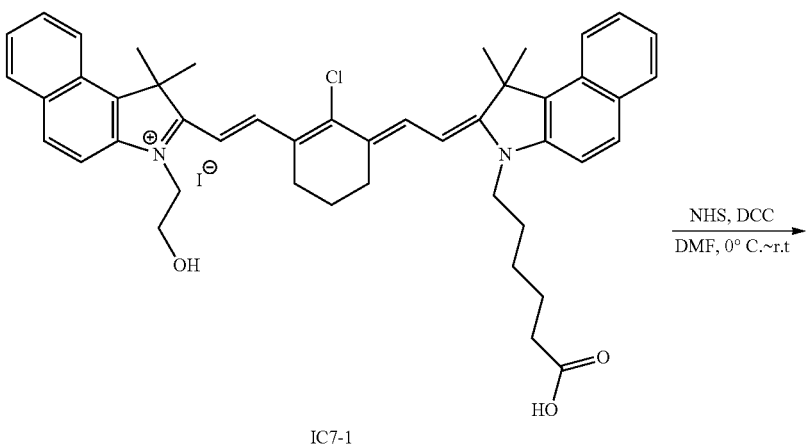

IC7-1    NHS, DCC / DMF, 0° C.~r.t →

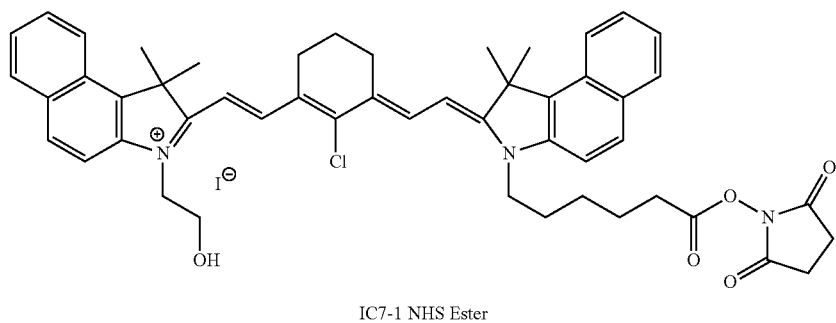

IC7-1 NHS Ester

Experimental Example 7: Synthesis of Aminated Poly-L-Lactic Acid and Aminated Poly-D-Lactic Acid In this experimental example, aminated poly-L-lactic acid (a-PLA) was synthesized using L-lactide (compound 6) and N-carbobenzoxy-1,2-diaminoethane hydrochloride (compound 7) (Scheme 7).

Scheme 7

[Chemical formula 34]

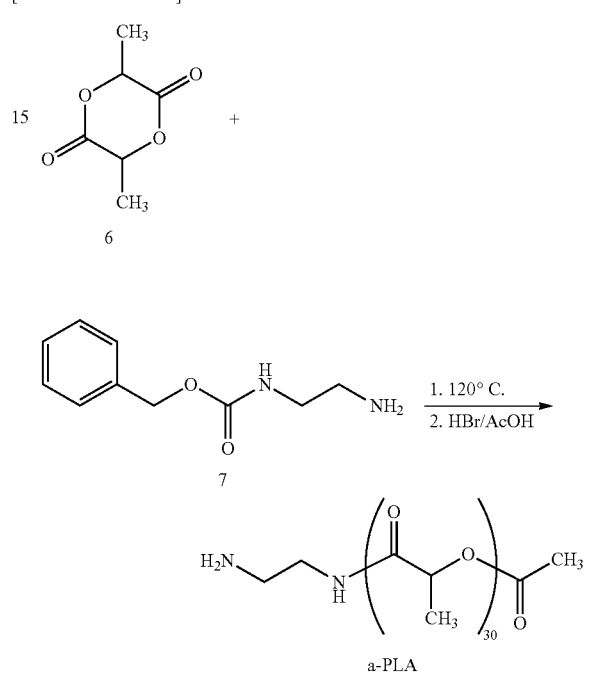

a-PLA

To N-carbobenzoxy-1,2-diaminoethane hydrochloride (compound 7) (310 mg, 1.60 mmol) served as a polymerization initiator, a dispersion liquid obtained by dispersing tin octanoate (6.91 mg) in toluene (1.0 mL) was added. The toluene was distilled away under reduced pressure, and then L-lactide (compound 6) (3.45 g, 24 mmol) was added to perform polymerization reaction at 120° C. under an Ar atmosphere. After 12 hours, the reaction container was air-cooled to room temperature to obtain a yellowish-white solid. The obtained yellowish-white solid was dissolved in a small amount of chloroform (about 10 mL). The resulting chloroform was dropped into cold methanol (100 mL) to obtain a white precipitate. The obtained white precipitate was collected by centrifugation and dried under reduced pressure.

To a dichloromethane (1 mL) solution of the obtained white precipitate (500 mg), 25 v/v % hydrogen bromide/acetic acid (2.0 mL) was added, and the mixture was stirred for 2 hours under dry air atmosphere in a shading environment. After the completion of reaction, the resultant reaction solution was dropped into cold methanol (100 mL) so that a precipitate was deposited. The precipitate was collected by centrifugation. The obtained white precipitate was dissolved in chloroform, washed with a saturated aqueous $NaHCO_3$ solution, and then dehydrated with anhydrous $MgSO_4$. Then, the $MgSO_4$ was removed by Celite® filtration, and the white precipitate was vacuum-dried to obtain white amorphous powder of a-PLA (440 mg).

Aminated poly-D-lactic acid was prepared in the same manner as described above except that D-lactide was used instead of L-lactide.

Experimental Example 8: Synthesis of Polylactic Acid-Bound Fluorescent Compounds (IC71-PLLA$_{30}$, ICG-PLLA$_{30}$ and Cy5-PLLA$_{30}$)

To a DMF solution containing 2.0 mg of a-PLA (1.0 eq), a DMF solution in which IC7-1 NHS ester, ICG-Sulfo-OSu, or Cy5 NHS ester was dissolved in an amount of 1.3 eq was added, and the mixture was stirred at room temperature for about 20 hours. Then, the mixture was purified using an LH20 column, and the solvent was distilled away under reduced pressure to obtain a polylactic acid-bound fluorescent compound. The synthesis scheme of IC71-PLLA$_{30}$ is shown in Scheme 8.

Scheme 8

[Chemical formula 35]

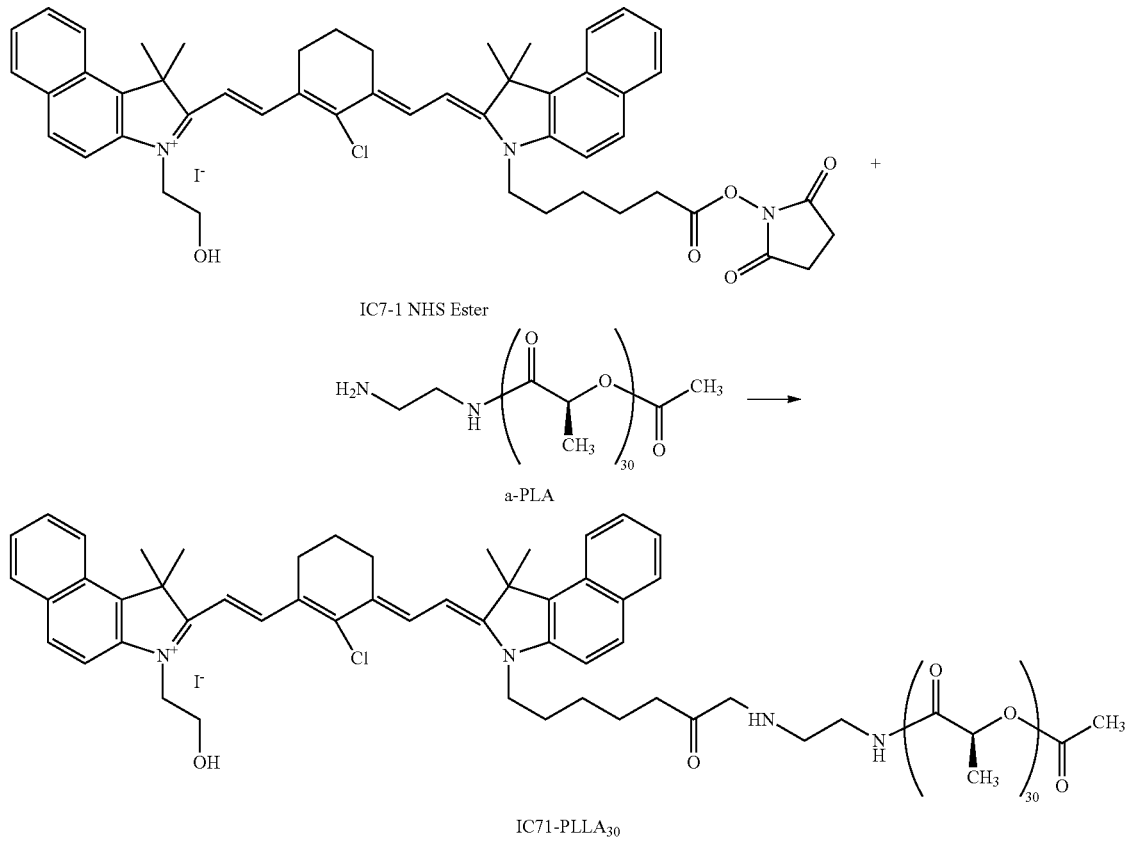

ICG-PLLA$_{30}$ and Cy5-PLLA$_{30}$ were prepared in the same manner as described above except that ICG-Sulfo-OSu and Cy5 NHS ester were used instead of IC7-1 NHS ester, respectively.

Experimental Example 9: Synthesis of Polysarcosine-Polylactic Acid Amphiphilic Block Polymer (PSar$_{70}$-PLLA$_{30}$)

In this experimental example, a polysarcosine-polylactic acid amphiphilic block polymer (PSar$_{70}$-PLLA$_{30}$) was synthesized from sarcosine-NCA (Sar-NCA) and aminated poly-L-lactic acid (a-PLA) (Scheme 9).

Scheme 9

[Chemical formula 36]

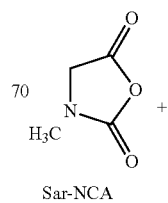

Sar-NCA

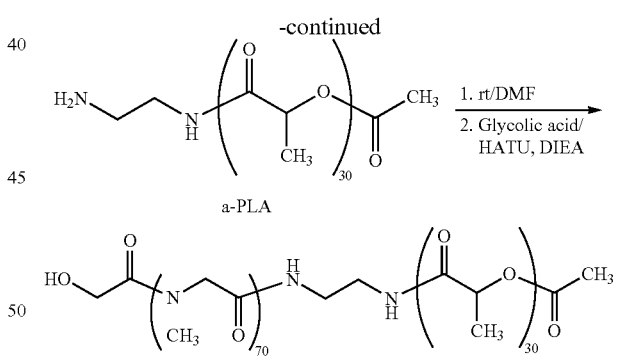

Dimethylformamide (DMF) (140 mL) was added to a-PLA (383 mg, 0.17 mmol) and sarcosine-NCA (Sar-NCA) (3.21 g, 27.9 mmol) under an Ar atmosphere, and the mixture was stirred at room temperature for 12 hours. After the reaction solution was cooled to 0° C., glycolic acid (72 mg, 0.95 mmol), O-(benzotriazol-1-yl)-N,N,N',N'-tetramethyluronium hexafluorophosphate (HATU) (357 mg, 0.94 mmol), and N,N-diisopropylethylamine (DIEA) (245 μL, 1.4 mmol) were added to the reaction solution, and reaction was performed at room temperature for 18 hours.

After DMF was distilled away under reduced pressure by a rotary evaporator, purification was performed using an LH20 column. Fractions showing a peak detected at CV 270 nm were collected and concentrated. The thus obtained concentrated solution was dropped into diethyl ether at 0° C. for reprecipitation to obtain PSar$_{70}$-PLLA$_{30}$ (1.7 g) as a target substance.

Experimental Example 10: Synthesis of NH-Polysarcosine-Polylactic Acid Amphiphilic Block Polymer (NH-PSar$_{56}$-PLLA$_{30}$)

Dimethylformamide (DMF) (140 mL) was added to a-PLA (1.48 g, 0.654 mmol) and sarcosine-NCA (Sar-NCA) (7.53 g, 6.54 mmol) under an Ar atmosphere, and the mixture was stirred at room temperature for 12 hours. After DMF was distilled away under reduced pressure by a rotary evaporator, purification was performed using an LH20 column. Fractions showing a peak detected at UV270 nm were collected and concentrated. The thus obtained concentrated solution was dropped into diethyl ether at 0° C. for reprecipitation to obtain target NH-PSar$_{56}$-PLLA$_{30}$ (4.7 g).

Example 1: Production of Nanoparticles Encapsulating Fluorescent Dye

A molecular assembly that is a carrier part of a nanoparticle and is composed of a polysarcosine-polylactic acid amphiphilic block polymer is referred to as a lactosome. Further, a molecular assembly composed of an antibody-modified polysarcosine-polylactic acid amphiphilic block polymer is referred to as an antibody-modified lactosome.

Example 1-1: Preparation-1 of Lactosome Encapsulating Fluorescent Dye

In this example, lactosomes encapsulating ICG-PLLA$_{30}$ or ICG-PDLA$_{32}$ as a fluorescent dye were prepared in the following manner.

A chloroform solution (0.2 mM) of a polylactic acid-polysarcosine amphiphilic block polymer (PSar$_{70}$-PLLA$_{30}$·26H$_2$O, MW=7,767) as a carrier agent, and a chloroform solution (0.2 mM) of each of the above-mentioned fluorescent dyes were prepared. In the case of each of the fluorescent dyes ICG-PLLA$_{30}$ and ICG-PDLA$_{32}$, both the solutions were mixed in a glass container so that the molarity of the fluorescent dye was 0.6 mol %, 1 mol %, 1.5 mol %, 2 mol %, 3 mol %, 4 mol %, or 5 mol %, respectively. Further, in the case of the fluorescent dye ICG-PLLA$_{30}$, both the solutions were mixed in a glass container so that the molarity of the fluorescent dye was 8 mol %. Then, each of lactosomes was produced according to a film method. The film method was performed in the following manner. The solvent was distilled away from the mixed solution under reduced pressure to form a film containing the carrier agent and the fluorescent dye on the wall surface of the glass container. Further, water or a buffer solution was added to the glass container having the film formed therein, and the glass container was put in hot water at 82° C. for 20 minutes and was then allowed to stand at room temperature for 30 minutes, and the water or buffer solution was filtered with a 0.2 mm filter and freeze-dried.

Example 1-2: Preparation-2 of Lactosome Encapsulating Fluorescent Dye

In this example, lactosomes encapsulating, as a fluorescent dye, IC71-PLLA$_{30}$, ICG-PLLA$_{30}$, IC7-1 (for comparison), or ICG (for comparison) were prepared in the following manner.

A chloroform solution (0.2 mM) of a polylactic acid-polysarcosine amphiphilic block polymer (PSar$_{70}$-PLLA$_{30}$·26H$_2$O, MW=7,767) as a carrier agent, and a chloroform solution (0.2 mM) of each of the above-mentioned fluorescent dyes were prepared. Both the solutions were mixed in a glass container so that the molarity of the fluorescent dye was 20 mol %, respectively. Then, the same manner as in Example 1-1 was performed according to the film method.

Example 1-3: Preparation-1 of Antibody-Modified Lactosome Encapsulating Fluorescent Dye In this example, an antibody-modified lactosome (anti HER2 scFv-lactosome) encapsulating IC71-PLLA$_{30}$ as a fluorescent dye was prepared in the following manner.

In 2.5 mL of dried dimethylformamide (DMF) was dissolved 100 mg of NH-PSar$_{56}$-PLLA$_{30}$, and then 21.3 mg (5 eq) of N-succimidyl 3-maleimidopropyonate (NSMP) and 5.45 μL (2 eq) of diisopropylethylamine (DIEA) were added, and the mixture was stirred at room temperature for 7 hours (Scheme 10). After DMF was distilled away, the resulting white precipitate was washed three times with ethyl acetate to obtain maleimide-modified PSar$_{56}$-PLLA$_{30}$ (yield: 59.1 mg). The maleimide-modified PSar$_{56}$-PLLA$_{30}$ was mixed with PSar$_{72}$-PLLA$_{30}$ in a ratio (molar ratio) of 1:1, and then IC71-PLLA$_{30}$ was added, and a maleimide lactosome was prepared according to the film method.

Scheme 10

[Chemical formula 37]

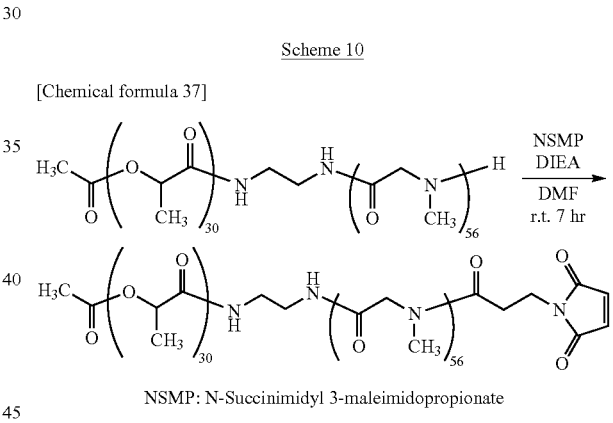

NSMP: N-Succinimidyl 3-maleimidopropionate

An anti HER2 single-chain antibody (anti HER2 scFV) was prepared using an *Escherichia coli* expression system, and purified using IMAC Kit (manufactured by Bio-Rad Laboratories) according to the attached protocol. To 100 μL of anti HER2 scFv (3 mg/mL PBS) was added 63.7 μg (10 eq) of tris(2-carboxyethyl)phosphine HCL (TCEP), and the mixture was stirred for 2 hours while cooled in ice. The mixture was purified using a spin column (Sephadex G-50; manufactured by GE Healthcare), and then 1 mL of the above maleimide lactosome (1 mg/mL PBS) was added, and the mixture was allowed to react for 4 hours while cooled in ice. Further, 50 μL of Cysteine.HCl (20 mM PBS) was added, and the mixture was stirred for 30 minutes while cooled in ice. Then, the mixture was purified using Amicon (100 kDa cut) (manufactured by Millipore Corporation). The obtained anti HER2 scFv-lactosome was analyzed using a size-exclusion column (Superdex 200 10/300 GL; manufactured by GE Healthcare). Further, the antibody bound to the lactosome was quantified using BCA Protein Assay Kit (manufactured by Thermo Scientific Inc.). The particle size of the obtained antibody-modified lactosome encapsulating a fluorescent dye was 38.5 nm (intensity), and the number of antibody molecules bound to the lactosome was 10/lactosome.

Example 1-4: Preparation-3 of Lactosome Encapsulating Fluorescent Dye

In this example, lactosomes encapsulating a fluorescent dye in which the molarity of fluorescent dye Cy5-PLLA$_{30}$ was 1 mol % or 20 mol % were prepared, respectively, in the same manner as in Examples 1-1 and 1-2 except that a polylactic acid-bound cyanine compound Cy5-PLLA$_{30}$ was used as a fluorescent dye.

Example 1-5: Preparation-2 of Antibody-Modified Lactosome Encapsulating Fluorescent Dye In this example, an antibody-modified lactosome encapsulating Cy5-PLLA$_{30}$ (Cy5 anti HER2 lactosome) was prepared in the same manner as in Example 1-3 except that a polylactic acid-bound cyanine compound Cy5-PLLA$_{30}$ was used as a fluorescent dye.

Example 2: Fluorescence Spectra of Lactosomes Encapsulating Fluorescent Dye

The freeze-dried products of the lactosomes (ICG-PLLA$_{30}$/lactosomes, ICG-PDLA$_{32}$/lactosomes) obtained in Example 1-1 each encapsulating 0.6 mol %, 1 mol %, 1.5 mol %, 2 mol %, 3 mol %, and 4 mol % of the fluorescent dye ICG-PLLA$_{30}$ or ICG-PDLA$_{32}$, respectively, and the freeze-dried product of the lactosome obtained in Example 1-1 encapsulating 8 mol % of the fluorescent dye ICG-PLLA$_{30}$ were subjected to fluorescence spectral measurement in the following manner. The measurement of fluorescence spectral in the range of 750 to 900 nm was performed using a fluorescence spectrophotometer (RF-5300PC manufactured by SHIMADZU CORPORATION) at an excitation wavelength of 730 nm.

Each of the lactosomes was dispersed in ultrapure water so that the concentration of the amphiphilic polymer was 1 mg/mL, and then the dispersion was diluted so that the concentration of the fluorescent agent was 0.48 µM, and was subjected to fluorescence spectral measurement (FIGS. 1(A) and 1(B)). In FIGS. 1(A) and 1(B), the horizontal axis represents wavelength and the vertical axis represents fluorescence intensity. Further, FIG. 1(C) shows the reduction of the fluorescence intensity of each lactosome at 817 nm. In FIG. 1(C), the vertical axis represents fluorescence intensity. As a result, it was found that the fluorescence intensity was reduced when the amount of encapsulated ICG-PLLA$_{30}$ or ICG-PDLA$_{32}$ was 1 mol % or more. In the case of ICG-PLLA$_{30}$, the fluorescence intensity had a tendency to be reduced to ½ every time the fluorescent dye content was increased by 3.7 mol %, and in the case of ICG-PDLA$_{32}$, the fluorescence intensity had a tendency to be reduced to ½ every time the fluorescent dye content was increased by 2.8 mol %.

Therefore, it was apparent that fluorescence quenching occurred in the lactosome in which a polylactic acid-bound cyanine compound was encapsulated at a high density.

Example 3: Change in Fluorescence Intensity of Lactosome Encapsulating Fluorescent Dye Due to Change in External Environment 1

Each lactosome (1 mg/mL) encapsulating 20 mol % of IC71 (for comparison), IC71-PLLA$_{30}$, ICG (for comparison), or ICG-PLLA$_{30}$ was mixed with phosphate buffered saline (PBS: composition of 29 g of Na$_2$HPO$_4$.12H$_2$O, 2.96 g of NaH$_2$PO$_4$.2H$_2$O, and 8.7 g of NaCl per one liter of ultrapure water), plasma (collected from male ddY mice), 5 wt % albumin (BSA), or 5 wt % SDS (dodecyl sodium sulfate) in a ratio (by volume) of 1:1, respectively; and the mixture was allowed to stand at room temperature for 30 minutes under lightproof conditions, and then diluted with PBS so that the concentration of the amphiphilic block polymer was ⅟15 mg/mL, and was subjected to fluorescence spectral measurement (FIGS. 2(A) to 2(D)). In FIGS. 2(A) to 2(D), the horizontal axis represents wavelength and the vertical axis represents fluorescence intensity. As a result, in the case of polylactic acid-unbound IC7-1 and polylactic acid-unbound ICG, the fluorescence intensity was recovered in the SDS solution, the plasma, and the BSA solution. On the other hand, in the case of polylactic acid-bound IC71-PLLA$_{30}$ and polylactic acid-bound ICG-PLLA$_{30}$, fluorescence remained quenched in the plasma and the BSA solution, and the fluorescence intensity was recovered only in the SDS solution. It is considered that SDS is a surfactant and therefore the structure of a lactosome particle is changed so that the fluorescence intensity is recovered.

Example 4: Temporal Change in Fluorescence Intensity of Lactosome Encapsulating Fluorescent Dye Due to Change in External Environment 2

Figure 3:
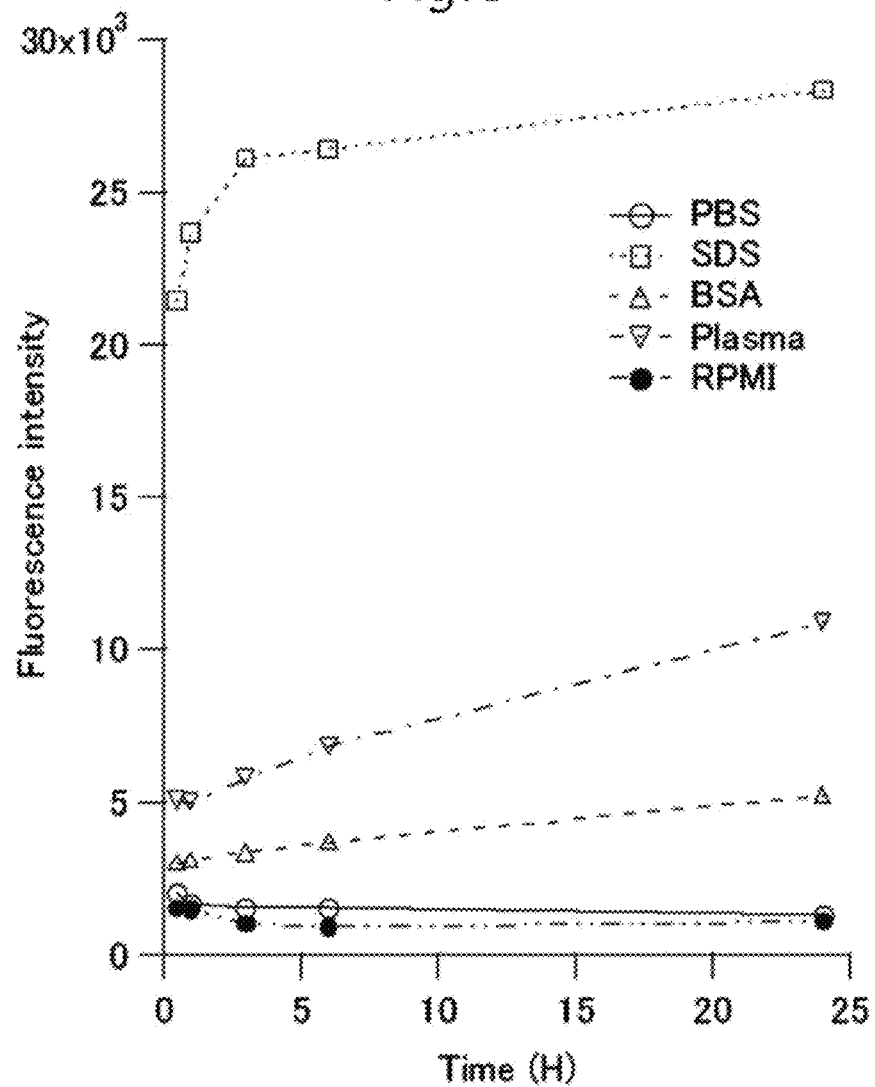
FIG. 3 shows temporal changes in the fluorescence intensity of lactosome encapsulating 20 mol % of IC71-PLLA$_{30}$ by changing an external environment, obtained in Example 4.

A lactosome encapsulating 20 mol % of IC71-PLLA$_{30}$ (1 mg/mL) was mixed with PBS, 5 wt % SDS, 5 wt % BSA, plasma, or RPMI (Roswell Park Memorial Institute) 1640 medium in a ratio (by volume) of 1:1, and the mixture was allowed to stand at room temperature for 30 minutes, 1 hour, 3 hours, 6 hours, and 24 hours under lightproof conditions, and then diluted with PBS so that the concentration of the amphiphilic block polymer was ⅟30 mg/mL, and was subjected to fluorescence spectral measurement (FIG. 3). In FIG. 3, the horizontal axis represents time (H) and the vertical axis represents fluorescence intensity. As a result, the fluorescence intensity was not changed in PBS and RPMI1640 medium even after 24 hours, and fluorescence remained quenched. The fluorescence intensities in BSA and plasma after 24 hours were 1.7 times and 2.2 times higher than those after 30 minutes, respectively. The fluorescence intensity in SDS was increased for up to 3 hours, and was then constant for up to 24 hours.

Example 5-1: Recovery of Fluorescence Intensity 1 (In Vitro)

Figure 4:
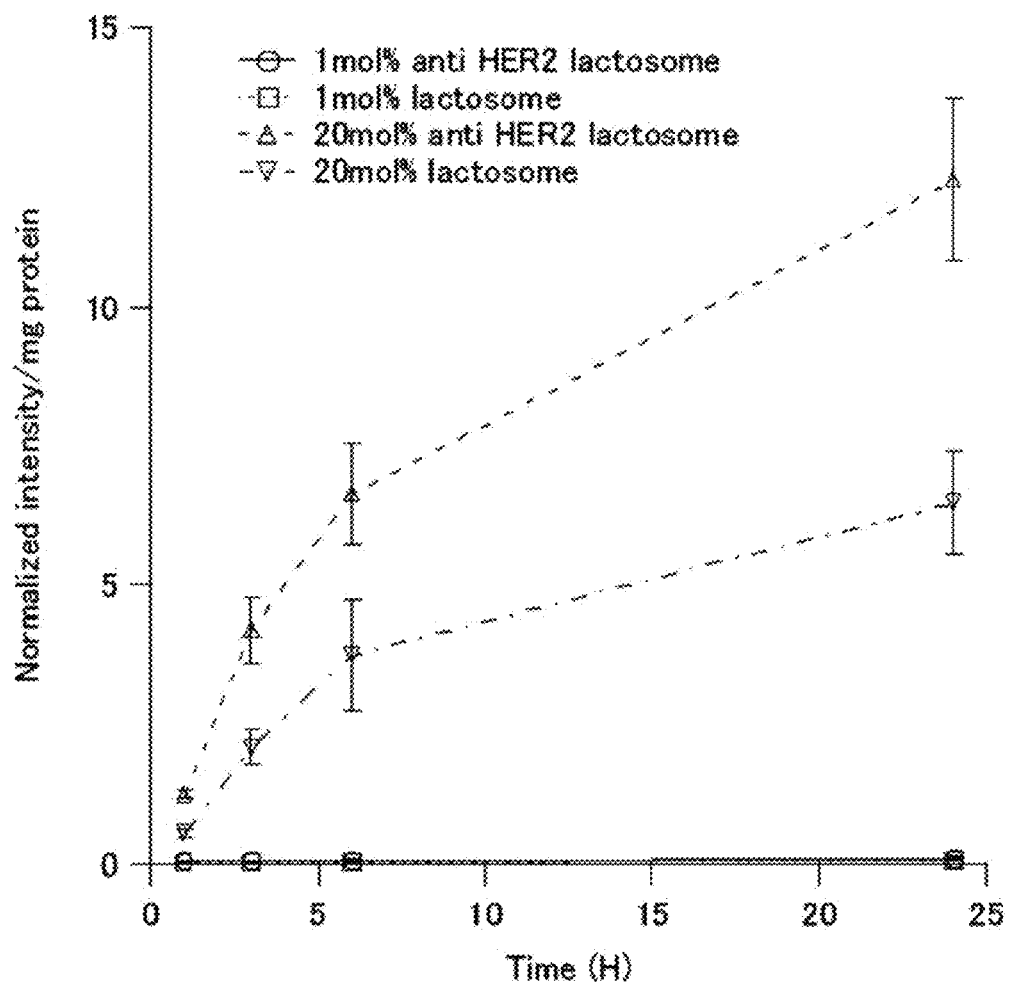
FIG. 4 shows the measurement results of fluorescence spectra obtained in Example 5-1, when lactosomes encapsulating 1 mol % or 20 mol % of IC71-PLLA$_{30}$ and antibody-modified lactosomes encapsulating 1 mol % or 20 mol % of IC71-PLLA$_{30}$ were brought into contact with or incorporated into cells.

N87 cells that express HER2 were added at 1×10$^5$ cells per well of 12-well plate, cultured overnight, and washed twice with PBS. An anti HER2 scFv-lactosome encapsulating 1 mol % or 20 mol % of IC71-PLLA$_{30}$ and a lactosome encapsulating 1 mol % or 20 mol % of IC71-PLLA$_{30}$ (40 µg/mL RPMI1640) was added at 1 mL/well, respectively. The cells were incubated at 37° C. in 5% CO$_2$ under lightproof conditions, and washed twice with PBS 30 minutes, 1 hour, 3 hours, 6 hours, and 24 hours after the start of the incubation. The fluorescence image of the cells in each well was taken after washing with PBS with the use of Clairvivo OPT (manufactured by SHIMADZU CORPORATION) (excitation: 785 nm, fluorescence: 845 nm, exposure time: 20 seconds (1 mol %), 5 seconds (20 mol %)). The results are shown in FIG. 4. In FIG. 4, the horizontal axis represents time (H) and the vertical axis represents fluorescence intensity (Normalized intensity/mg protein). The normalized intensity is a value obtained by dividing the fluorescence intensity of the cells by the fluorescence intensity of the solution added.

As shown in FIG. 4, in the case of the surface-unmodified lactosome, the fluorescence intensity measured 24 hours after the addition was about 93 times higher when 20 mol % of the polylactic acid-bound cyanine compound was encapsulated than when 1 mol % of the polylactic acid-bound cyanine compound was encapsulated. On the other hand, in the case of the anti HER2 scFv-modified lactosome, the fluorescence intensity measured 24 hours after the addition was about 120 times higher when 20 mol % of the polylactic acid-bound cyanine compound was encapsulated than when 1 mol % of the polylactic acid-bound cyanine compound was encapsulated. The reason why the fluorescence intensity was higher when the anti HER2 scFv-modified lactosome was added is considered as follows: anti HER2 scFv binds to HER2 expressed on the surface of the cells, and therefore the anti HER2 scFv-modified lactosome is more likely to be incorporated into the cells.

Example 5-2: Recovery of Fluorescence Intensity 2
(In Vitro)

In this example, incorporation of an antibody-modified lactosome (Cy5 anti HER2 lactosome) encapsulating 1 mol % of a polylactic acid-bound cyanine compound Cy5-PLLA$_{30}$ as a fluorescent dye, or an antibody-unmodified lactosome (Cy5 lactosome) encapsulating 1 mol % of the Cy5-PLLA$_{30}$ into cells was evaluated using a fluorescence microscope.

N87 cells were added at 1×10$^5$ cells per 3.5 cm glass base dish (IWAKI), cultured overnight, and washed twice with PBS. A Cy5 anti HER2 lactosome (40 μg/mL RPMI) or a Cy5 lactosome (40 μg/mL RPMI) was added as a lactosome solution at 1 mL/well. The lactosome solution was removed 1 hour, 3 hours, 6 hours, and 24 hours after the addition of the each lactosome solution, and the cells were washed twice with PBS and observed under a fluorescence microscope (BZ9000, KEYENCE). The results of fluorescent observation of the antibody-modified lactosome (HER2 lactosome) and the antibody-unmodified lactosome (lactosome) are shown in FIG. 5(A) and FIG. 5(B), respectively, together with bright-field images (lower images). As shown in FIG. 5, it was found that, even when the lactosome was not modified with an antibody, the antibody-unmodified lactosome was incorporated into the cells 24 hours after the addition of the lactosome. It was also found that when the lactosome was modified with the antibody, fluorescence was observed at the cell membrane 1 hour after the addition of the lactosome, and the antibody-modified lactosome was slowly localized in the cells.

Example 5-3: Recovery of Fluorescence Intensity 3
(In Vitro)

In this example, incorporation of an antibody-modified lactosome (Cy5 anti HER2 lactosome) encapsulating 20% of a polylactic acid cyanine compound Cy5-PLLA$_{30}$ as a fluorescent dye, or an antibody-unmodified lactosome (Cy5 lactosome) encapsulating 20 mol % of the Cy5-PLLA$_{30}$ into cells was evaluated in more detail using a fluorescence microscope.

N87 cells were added at 1×10$^5$ cells per 3.5 cm glass base dish (IWAKI), cultured overnight, and washed twice with PBS. An antibody-modified lactosome: Cy5 anti HER2 lactosome (40 μg/mL RPMI) or an antibody-unmodified lactosome: Cy5 lactosome (40 μg/mL RPMI) was added as a lactosome solution at 1 mL/well. The lactosome solution was removed 3 hours, 6 hours, and 24 hours after the addition of the each lactosome solution, and the cells were washed twice with PBS. Further, the cells were stained with Hoechst 33342 (DOJINDO LABORATORIES) as a cell nuclei stain and Lyso Tracker Yellow HCK-123 (Invitrogen) as a lysosome stain, and observed under a fluorescence microscope (BZ9000, KEYENCE).

The results of comparative observation of the stained cells and the cells in which fluorescence was observed are shown in FIG. 6. FIG. 6(A) shows the photographs of the cells into which the antibody-modified lactosome (HER2 lactosome) was incorporated, and FIG. 6(B) shows the photographs of the cells into which the antibody-unmodified lactosome (lactosome) was incorporated, and these photographs were taken during bright-field observation, observation of fluorescence from Hoechst 33342, observation of fluorescence from Lyso Tracker Yellow HCK-123, and observation of fluorescence from Cy5.

As shown in FIG. 6, fluorescence from Cy5 is localized at the same sites in the cells as fluorescence from Lyso Tracker. Therefore, it is considered that the lactosome incorporated into the cells was incorporated into lysosomes and decomposed by enzymes present in the lysosomes so that fluorescence was recovered. Further, it was suggested that the lactosome was not incorporated into cell nuclei.

Example 5-4: Recovery of Fluorescence Intensity 4
(In Vitro)

N87 cells, BT-474 cells, and SK-BR-3 cells that express HER2 and MCF-7 cells that do not express HER2 were added at 1×10$^5$ cells per well of 12-well plate, respectively, cultured overnight, and washed twice with PBS. A HER2 antibody-modified lactosome (anti HER2 lactosome) encapsulating 20 mol % of IC71-PLLA$_{30}$ (40 μg/mL RPMI1640) or an antibody-unmodified lactosome (lactosome) encapsulating IC71-PLLA$_{30}$ (40 μg/mL RPMI1640) was added at 1 mL/well, respectively. The cells were incubated at 37° C. in 5% CO$_2$ under lightproof conditions, and washed twice with PBS 1 hour, 3 hours, 6 hours, and 24 hours after the start of the incubation. The fluorescence image of the cells in each well was taken after washing with PBS with the use of Clairvivo OPT (manufactured by SHIMADZU CORPORATION) (excitation: 785 nm, fluorescence: 845 nm, exposure time: 5 seconds). In the case of N87 cells, BT-474 cells, and SK-BR-3 cells that express HER2, a competitive inhibition experiment was further performed by adding anti HER2 antibody alone in an amount of 100 equivalents with respect to the antibody-modified lactosome, and fluorescence images were taken.

The measurement results of fluorescence spectral are shown in FIG. 7. In FIG. 7, the horizontal axis represents time (hr) and the vertical axis represents fluorescence intensity (normalized intensity/mg protein). The normalized intensity is a value obtained by dividing the fluorescence intensity of the cells by the fluorescence intensity of the solution added. In FIG. 7, "anti HER2 lactosome" represents the result when the antibody-modified lactosome encapsulating IC71-PLLA$_{30}$ was used, "anti HER2 lactosome (inhibition)" represents the result of the competitive inhibition experiment, and "lactosome" represents the result when the antibody-unmodified lactosome encapsulating IC71-PLLA$_{30}$ was used.

As shown in FIG. 7, when N87 cells, BT-474 cells, and SK-BR-3 cells that express HER2 were used, the recovery ratio of fluorescence intensity was higher when the HER2 antibody-modified lactosome was added; and when MCF-7 cells that do not express HER2 were used, the recovery ratio of fluorescence intensity was similar regardless of the presence or absence of an antibody label. When anti HER2 antibody was added to perform a competitive inhibition experiment, the recovery ratio of fluorescence intensity of the HER2 antibody-modified lactosome was reduced, which indicates that the HER2 antibody-modified lactosome was incorporated into the cells by interaction with HER2 expressed on the surface of the cells.

Example 6: Recovery of Fluorescence Intensity (In Vivo)

N87 cells were transplanted into the right lower limbs of 4-week-old female Balb/c nude mice, and 3 to 4 weeks after the transplantation, 0.1 mL of 1 mol % or 20 mol % IC71-PLLA$_{30}$ anti HER2 scFv-lactosome (2 mg/mL PBS) was administered to the mice via tail vein, and the fluorescence images of the mice were taken immediately and 1, 3, 6, 9, 12, and 24 hours after the administration with the use of Clairvivo OPT (manufactured by SHIMADZU CORPORATION) (excitation: 785 nm, fluorescence: 845 nm, exposure time: 10 seconds (1 mol %), 5 seconds (20 mol %)).

The results of fluorescence imaging of the above cancer-bearing mice are shown in FIG. 8. The intensity of fluorescence was illustrated in the range of 40 to 100% when the fluorescence intensity of a tumor site measured 24 hours after the administration was taken as 100%. After the administration, the fluorescence intensity of the tumor site in the right lower limb was gradually increased both when 1 mol % of IC71-PLLA$_{30}$ was encapsulated (FIG. 8(A)) and when 20 mol % of IC71-PLLA$_{30}$ was encapsulated (FIG. 8(B)). In the case of the above fluorescence intensity range, fluorescence was observed just after the administration when 1 mol % of IC71-PLLA$_{30}$ was encapsulated, but fluorescence was not observed until 3 hours after the administration when 20 mol % of IC71-PLLA$_{30}$ was encapsulated. It is considered that the results indicate that when 20 mol % of IC71-PLLA$_{30}$ was encapsulated, the encapsulated fluorescent agent was more favorably quenched in the early stage of the administration.

Based on the results of fluorescence imaging shown in FIG. 8, temporal changes in the fluorescence intensity of the tumor site and of a background (specifically, of the back) are shown in FIG. 9(A) and FIG. 9(B), respectively. In FIG. 9, the horizontal axis represents time (H) and the vertical axis represents fluorescence intensity (counts/sec). As a result, increases in the fluorescence intensity were observed just after the administration. There was no difference in fluorescence intensity for up to 1 hour after the administration between when the 1 mol % IC71-PLLA$_{30}$ anti HER2 scFv-lactosome was administered and when the 20 mol % IC71-PLLA$_{30}$ anti HER2 scFv-lactosome was administered. However, in the latter case, the fluorescence intensity of the tumor site was rapidly increased 3 to 24 hours after the administration. When 1 mol % of IC71-PLLA$_{30}$ was encapsulated, the fluorescence intensity of the tumor site measured just after the administration was about 49% of that measured 24 hours after the administration; and when 20 mol % of IC71-PLLA$_{30}$ was encapsulated, the fluorescence intensity of the tumor site measured just after the administration was about 5.7% of that measured 24 hours after the administration. The results indicate that in both cases, the quenched fluorescent agent was switched into an on-state by contact with the cells as the off-state nanoparticles that remained quenched in blood accumulated in the tumor by the EPR effect.

FIG. 10 shows temporal changes in the fluorescence intensity ratio (T/B ratio) between the tumor site and the background. In FIG. 10, the horizontal axis represents time (H) and the vertical axis represents the fluorescence intensity ratio (tumor/background ratio) between the tumor site and the background. As a result, increases in the T/B ratio were observed. It was shown that the T/B ratio was higher when 20 mol % of the fluorescent agent was encapsulated than when 1 mol % of the fluorescent agent was encapsulated. The difference in the T/B ratio between when 1 mol % of the fluorescent agent was encapsulated and when 20 mol % of the fluorescent agent was encapsulated was largest 3 hours after the administration, and more specifically, the T/B ratio was about 1.4 times higher when 20 mol % of the fluorescent agent was encapsulated than when 1 mol % of the fluorescent agent was encapsulated. In both cases, the reason for the increase in the T/B ratio is considered as follows: the quenched fluorescent agent was switched into an on-state by contact with the cells after the off-state nanoparticles accumulated in the tumor by the EPR effect.

It is to be noted that when a probe that is always in an on-state is administered, the fluorescence intensity of the background is reduced with time dependently on blood concentration thereof, but as shown in FIG. 9(B), when 20 mol % IC71-PLLA$_{30}$ anti HER2 scFv-lactosome was administered, an increase in the fluorescence intensity of the background was also observed 3 hours after the administration. The reason for the results is considered to be because the lactosome was decomposed also in blood. However, it took time to decompose the lactosome in blood, and the lactosome was delivered to a tumor by EPR etc. during a quenched state and therefore the amount of the lactosome retained in blood was reduced. As a result, it is considered that the T/B ratio was higher when the 20 mol % of IC71-PLLA$_{30}$ anti HER2 scFv-lactosome was administered than when the 1 mol % IC71-PLLA$_{30}$ anti HER2 scFV-lactosome was administered.

The invention claimed is:

1. A fluorescent nanoparticle probe comprising:
   a molecular assembly composed of an amphiphilic block polymer having a hydrophilic block chain and a hydrophobic block chain; and
   a fluorescent dye encapsulated in the molecular assembly, wherein
   (a) an essential hydrophilic structural unit is defined as a unit selected from a sarcosine unit and an alkylene oxide unit, and the hydrophilic block chain has 20 or more essential hydrophilic structural units,
   (b) an essential hydrophobic structural unit is defined as a unit selected from the group consisting of an amino acid unit and a hydroxylic acid unit, and the hydrophobic block chain has 15 or more essential hydrophobic structural units, and
   (c) the fluorescent dye is a polylactic acid-bound cyanine compound comprising:
   a fluorescent group represented by the following structural formula (I):

[Chemical Formula 1]

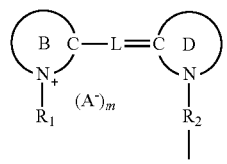
(I)

wherein $R_1$ is a hydrocarbon group which may be substituted, and $R_2$ is a bivalent hydrocarbon group which may be substituted; A' is an anion and m is 0 or 1; a ring B and a ring D may be the same or different from each other and each is a nitrogen-containing heterocycle; and L is a linking group that constitutes a polymethine chain, which may include a ring structure, and which may be substituted; and a polylactic acid group having 5 to 50 lactic acid units, and two or more molecules of the fluorescent dye are encapsulated in a self-quenching state by association in the single molecular assembly, wherein the fluorescent dye is encapsulated in the molecular assembly in an amount of 5 to 20 mol % with respect to a total amount of the amphiphilic block polymer and the fluorescent dye so that the fluorescent nanoparticle remains self-quenching state by contact with a blood component.

2. The fluorescent nanoparticle probe according to claim 1, wherein the fluorescent dye is encapsulated in the molecular assembly in an amount of 10 to 20 mol % with respect to a total amount of the amphiphilic block polymer and the fluorescent dye.

3. The fluorescent nanoparticle probe according to claim 1, wherein fluorescence intensity when brought into contact with or incorporated into a cell is 10 times or more higher than that when brought into contact with a blood component.

4. The fluorescent nanoparticle probe according to claim 1, wherein the linking group represented by L has either of the following structures:

[Chemical Formula 2]

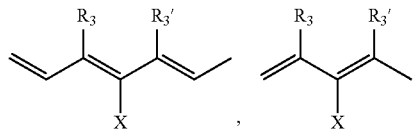

wherein $R_3$ and $R_3'$ are hydrogen or are linked together to form the ring structure; and X is hydrogen or a halogen.

5. The fluorescent nanoparticle probe according to claim 1, wherein the ring B has either of the following structures:

[Chemical Formula 3]

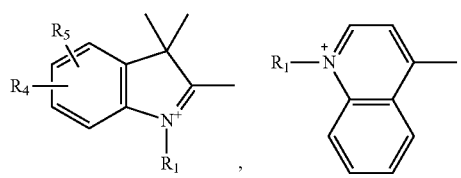

wherein $R_1$ is a hydrocarbon group which may be substituted; and $R_4$ and $R_5$ are each hydrogen or an anionic substituent group, or are linked together to form an aryl ring, and the ring D has either of the following structures:

[Chemical Formula 4]

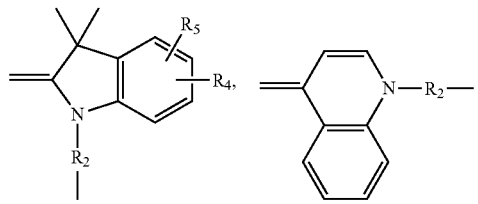

wherein $R_2$ is a bivalent hydrocarbon group which may be substituted; and $R_4$ and $R_5$ are each hydrogen or an anionic substituent group, or are linked together to form an aryl ring.

6. The fluorescent nanoparticle probe according to claim 1, wherein the fluorescent group is represented by the following structural formula (II):

[Chemical Formula 5]

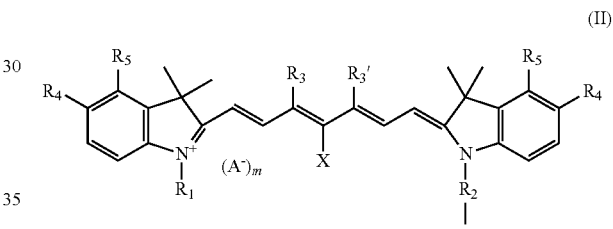
(II)

wherein $R_1$ is a hydrocarbon group which may be substituted, $R_2$ is a bivalent hydrocarbon group which may be substituted; $R_3$ and $R_3'$ are hydrogen or are linked together to form a ring structure; X is hydrogen or a halogen; A" is an anion and m is 0 or 1; and $R_4$ and $R_5$ are each hydrogen or an anionic substituent group or are linked together to form an aryl ring.

7. The fluorescent nanoparticle probe according to claim 1, wherein the fluorescent group is represented by the following structural formula (III):

[Chemical Formula 6]

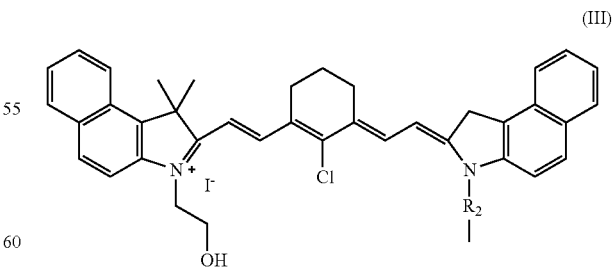
(III)

wherein $R_2$ is a bivalent hydrocarbon group which may be substituted.

8. The fluorescent nanoparticle probe according to claim 1, wherein the fluorescent group is represented by the following structural formula (IV):

[Chemical Formula 7]

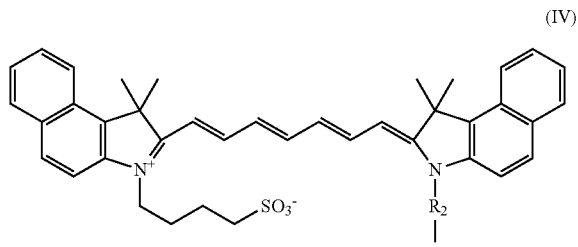

(IV)

wherein R₂ is a bivalent hydrocarbon group which may be substituted.

9. The fluorescent nanoparticle probe according to claim 1, wherein the fluorescent group is represented by the following formula (X):

[Chemical Formula 8]

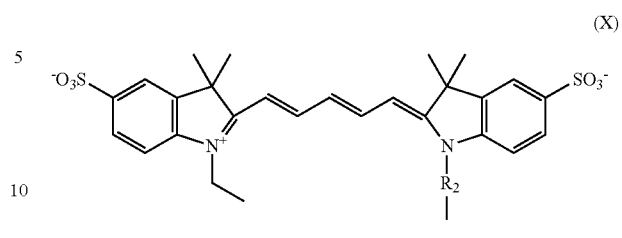

(X)

wherein R₂ is a bivalent hydrocarbon group which may be substituted.

10. The fluorescent nanoparticle probe according to claim 1, wherein the fluorescent dye is represented by the following formula (III-i):

[Chemical Formula 9]

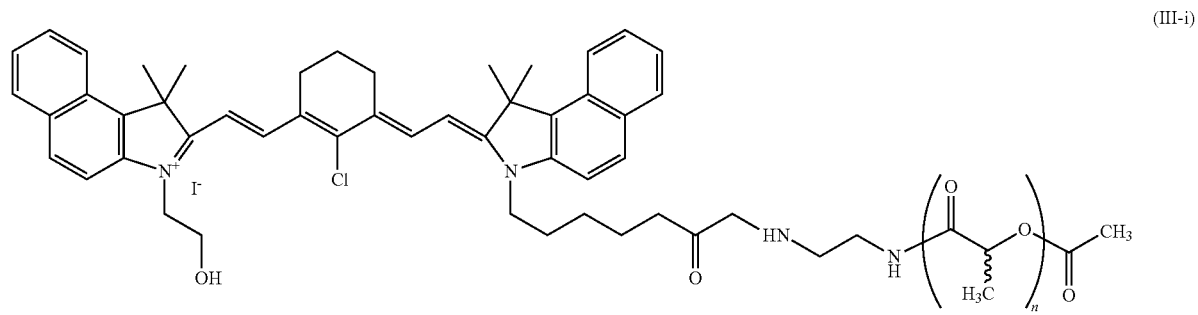

(III-i)

wherein n is an integer of 5 to 50.

11. The fluorescent nanoparticle probe according to claim 1, wherein the fluorescent dye is represented by the following formula (IV-i):

[Chemical Formula 10]

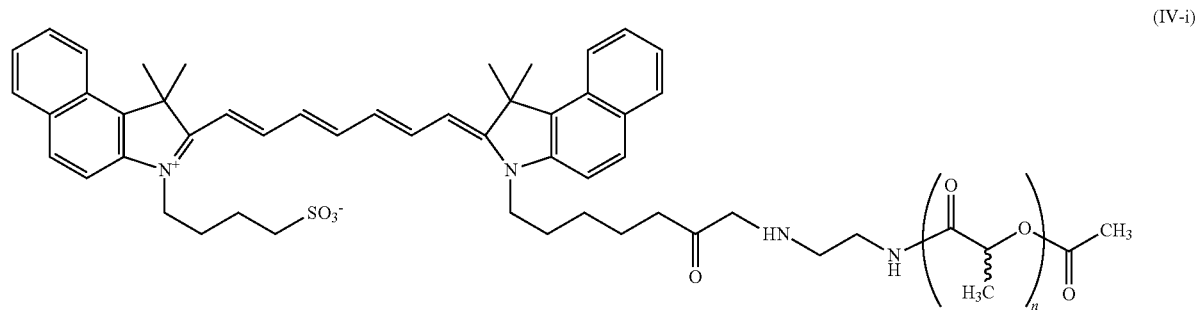

(IV-i)

wherein n is an integer of 5 to 50.

12. The fluorescent nanoparticle probe according to claim 1, wherein the fluorescent dye is represented by the following formula (X-i):

[Chemical formula 11]

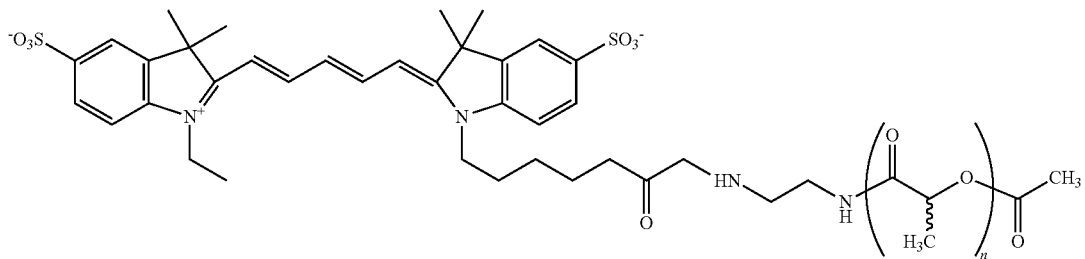

(X-i)

wherein n is an integer of 5 to 50.

13. The fluorescent nanoparticle probe according to claim 1, wherein the hydrophobic block chain is selected from the group consisting of:
- a hydrophobic polypeptide chain having 10 or more hydrophobic amino acid units,
- a hydrophobic polyester chain having 15 or more hydroxylic acid units, and
- a hydrophobic depsipeptide chain having a total of 20 or more units of both an amino acid unit and a hydroxylic acid unit.

14. The fluorescent nanoparticle probe according to claim 1, wherein the hydrophobic block chain is a hydrophobic block chain having 25 or more lactic acid units.

15. The fluorescent nanoparticle probe according to claim 1, wherein the hydrophilic block chain has an antibody, and a surface of the probe is modified with the antibody.

16. The fluorescent nanoparticle probe according to claim 15, wherein the antibody is an antibody against a substance contained in a tumor.

17. A fluorescent molecular imaging method comprising the steps of:
- administering the fluorescent nanoparticle probe according to claim 1 to a non-human animal; and
- detecting fluorescence.

* * * * *